US008062837B2

(12) United States Patent
Chow

(10) Patent No.: US 8,062,837 B2
(45) Date of Patent: Nov. 22, 2011

(54) PLASMA-DEPLETED, NOT ERYTHROCYTE-DEPLETED, CORD BLOOD COMPOSITIONS AND METHOD OF MAKING

(75) Inventor: Robert Chow, Irvine, CA (US)

(73) Assignee: StemCyte, Inc., Arcadia, CA (US)

( * ) Notice: Subject to any disclaimer, the term of this patent is extended or adjusted under 35 U.S.C. 154(b) by 0 days.

(21) Appl. No.: 11/422,017

(22) Filed: Jun. 2, 2006

(65) Prior Publication Data

US 2006/0275271 A1 Dec. 7, 2006
US 2008/0166324 A9 Jul. 10, 2008

Related U.S. Application Data

(60) Provisional application No. 60/733,956, filed on Nov. 3, 2005, provisional application No. 60/687,127, filed on Jun. 2, 2005.

(51) Int. Cl.
*A01N 1/02* (2006.01)
(52) U.S. Cl. ............................................................ 435/2
(58) Field of Classification Search ........................ None
See application file for complete search history.

(56) References Cited

U.S. PATENT DOCUMENTS

| | | | | |
|---|---|---|---|---|
| 4,735,726 | A | * | 4/1988 | Duggins ........................ 210/637 |
| 5,004,681 | A | | 4/1991 | Boyse et al. |
| 5,102,783 | A | | 4/1992 | Alkemade et al. |
| 5,192,553 | A | | 3/1993 | Boyse et al. |
| 5,372,581 | A | | 12/1994 | Anderson |
| 5,415,665 | A | | 5/1995 | Hessel et al. |
| 5,486,359 | A | | 1/1996 | Caplan et al. |
| 5,580,714 | A | * | 12/1996 | Polovina ........................ 435/2 |
| 5,789,147 | A | | 8/1998 | Rubinstein et al. |
| 5,916,602 | A | | 6/1999 | Klaus |
| 5,928,214 | A | * | 7/1999 | Rubinstein et al. ........... 604/410 |
| 5,993,387 | A | | 11/1999 | Moore et al. |
| 6,037,174 | A | | 3/2000 | Smith et al. |
| 6,461,645 | B1 | | 10/2002 | Boyse et al. |
| 6,569,427 | B1 | | 5/2003 | Boyse et al. |
| 6,605,275 | B1 | | 8/2003 | Boyse et al. |
| 2003/0039952 | A1 | | 2/2003 | Peled |
| 2003/0161818 | A1 | | 8/2003 | Weiss et al. |
| 2003/0180269 | A1 | | 9/2003 | Hariri |
| 2003/0215942 | A1 | | 11/2003 | Chow et al. |
| 2004/0071666 | A1 | | 4/2004 | Ferrara et al. |
| 2004/0197310 | A1 | | 10/2004 | Sanberg et al. |
| 2004/0219136 | A1 | | 11/2004 | Hariri |
| 2009/0016997 | A1 | | 1/2009 | Hathaway et al. |
| 2010/0189696 | A1 | | 7/2010 | Sun et al. |

FOREIGN PATENT DOCUMENTS

| | | |
|---|---|---|
| EP | 0 343 217 B1 | 5/1996 |
| WO | WO 89/04168 A1 | 5/1989 |
| WO | WO 00/38762 A1 | 7/2000 |
| WO | WO 00/73421 A2 | 12/2000 |
| WO | 03/068172 * | 8/2003 |
| WO | WO 2004/096319 A1 | 11/2004 |

OTHER PUBLICATIONS

Mamoury et al., "Cord Hemoglobin in Newborns in Correlation with Maternal Hemoglobin in Northeastern Iran", IJMS 28 (3) : 166-168 (2003).*
Clinical Hematology, 7th Edition, Wintrobe et al., eds. publisher Lea & Febiger, 1974, p. 1791.*
Ademokun et al., "Umbilical cord blood collection and separation for haematopoietic progenitor cell banking", Bone Marrow Transplantation 19 : 1023-1028 (1997).*
Woods et al., "A Theoretically Optimized Method for Cord Blood Stme Cell Cryopreservation", J. Hematotherapy & Stem Cell research 12 : 341-350 (2003).*
Rubinstein et al., "Processing and Cryopreservation of placental/umbilical cord blood for unrelated bone marrow reconstitution", PNAS 92 : 10119-10122 (1995).*
Armitage, S. et al., "Cord blood banking: volume reduction of cord blood units using a semi-automated closed system," Bone Marrow Transplantation, 1999, vol. 23, pp. 505-509.
Barker, J. et al., "Transplantation of 2 Partially HLA-matched Umbilical Cord Blood Units to Enhance Engraftment in Adults with Hematologic Malignancy." Blood, vol. 105 No. 3 (2005).
Bensinger, W. et al., "ABO-Incompatible Marrow Transplants." Transplantation, vol. 33 No. 4 (1982).
Broxemeyer, Hal E. et al, "Human umbilical cord blood as a potential source of transplantable hematopoietic stem/progenitor cells," Proc. Natl. Acad. Sci., 1989, vol. 86, pp. 3828-3832.
Broxmeyer, H.E., et al., "High-efficiency recovery of immature haematopoietic progenitor cells with extensive proliferative capacity from human cord blood cryopreserved for 10 years," Clin. Exp. Immunol, 1997, vol. 107 (Suppl. 1) pp. 45-53.
Broxmeyer, Hal et al., "High-efficiency recovery of functional hematopoietic progenitor and stem cells from human cord blood cryopreserved for 15 years," PNAS, 2003, vol. 100, No. 2, pp. 645-650.
Davey, Sue at al., "The London Cord Blood Bank: analysis of banking and transplantation outcome," British Journal of Haematology, 2004, vol. 125, pp. 358-365.
Dexter, T.M., et al., "Conditions Controlling the Proliferation of Haemopoietic Stem Cells In Vitro." J. Cell Physiol, 91:335-344. (1977).
Escolar, M. et al., "Transplantation of Umbilical-Cord Blood in Babies with Infantile Krabbe's Disease." NEJM, 352; 20. (2005).
Fasouliotis, Sozos et al., "Human umbilical cord blood banking and transplantation: a state of the art," European Journal of Obstetrics & Gynecology and Reproductive Biology, 2000, vol. 90, pp. 13-25.
Hahn, T. et al., "Infusion of Unwashed Umbilical Cord Blood Stem Cells after Thawing for Allogeneic Transplantation." Bone Marrow Transplantation, 34:739. (2004).

(Continued)

*Primary Examiner* — Sandra Saucier
(74) *Attorney, Agent, or Firm* — Kilpatrick Townsend & Stockton LLP

(57) ABSTRACT

The umbilical cord blood (UCB) compositions of the present invention possess the unique features of having plasma that is substantially depleted from the UCB unit and red blood cells (RBC) that are not depleted from the UCB unit. Such UCB units can be prepared by a process that combines plasma depletion with cryopreservation, selection, thawing, and/or transplantation of hematopoietic stem cells to provide superior clinical outcome by maximizing post-processing cell recovery and post-thaw infusion cell dose. Methods for treating a wide variety of malignant diseases and benign diseases associated with the hematopoietic system by administering the UCB compositions of the present invention are also provided.

30 Claims, 6 Drawing Sheets

OTHER PUBLICATIONS

Hahn, T. et al., "Use of Nonvolume-reduced (unmanipulated after thawing) Umbilical Cord Blood Stem Cells for Allogeneic Transplantation Results in Safe Engraftment." Bone Marrow Transplantation, 32:145-150. (2003).

Hahn, T. et al., "Cord Blood Stem Cells; Use of nonvolume-reduced (unmainpulated after thawing) umbilical cord blood stem cells for allogeneic transplantation results in safe engraftment," Bone Marrow Transplantation, 2003, vol. 31, pp. 145-150.

Kurtzberg, J. et al., "Placental Blood as a Source of Hematopoietic Stem Cells for Transplantation into Unrelated Recipients." NEJM, vol. 335 pp. 157-166 (1996).

Laughlin, Mary J. et al., "Outcomes after Transplantation of Cord Blood or Bone Marrow from Unrelated Donors in Adults with Leukemia." NEJM 351;2265 (2004).

Laughlin, MJ "Umbilical cord blood for allogeneic transplantation in children and adults," Bone Marrow Transplantation, 2001, vol. 27, pp. 1-6.

Locatelli, F. et al., "Factors Associated with Outcome after Cord Blood Transplantation in Children with Acute Leukemia." Blood, vol. 93 No. 11 (1999).

Nagamura-Inoue, T., et al., "Wash-out DMSO does not improve the speed of Engraftment of Cord Blood Transplantation: Follow-up of 46 Adult Patients with units Shipped from a single Cord Blood Bank." Transfusion, vol. 43 (2003).

Rocha, V. et al., "Transplants of Umbilical-Cord Blood or Bone Marrow from Unrelated Donors in Adults with Acute Leukemia." NEJM, 351:22 (2004).

Sauer-Heilborn, A. et al., "Patient Care During Infusion of Hematopoietic Progenitor Cells." Transfusion, vol. 44. pp. 907-916 (2004).

Smith, S. et al., "The Influence of Oxygen Tension on the Long-term growth in vitro of Haematopoietic Progenitor cells from Human Cord Blood." British Journal of Haematology, 63: 29-34 (1986).

Vicente, D. et al., "Progenitor cells Trapped in Marrow Filters can Reduce GvHD and Transplant Mortality." Bone Marrow Transplantation, 38: 111-117 (2006).

Wagner, J. et al., "Transplantation of Unrelated Donor Umbilical Cord Blood in 102 Patients with Malignant and Nonmalignant Diseases: Influence of CD34 cell dose and HLA Disparity on Treatment-related Morality and Survival." Blood, vol. 100 No. 5 (2002).

Whitlock, C. et al., "Long-term Culture of B Lymphocytes and their Presursors from Murine Bone Marrow." Proc. Natl. Acad. Sci. USA vol. 79, pp. 3608-3612 (1982).

Ballen, Karen K., "New trends in umbilical cord blood transplantation," Blood, 2005, vol. 105, No. 10, pp. 3786-3792.

Chow et al., "Clinical Outcome of Hematopoietic Stem Cell Transplantation (HSCT) using plasma depleted umbilical cord blood units (UCB) that were not depleted of red blood cells prior to cryopreservation," Blood, 2005, vol. 106, No. 11, pp. 578A-579A.

Chow et al., "Hematopoietic Stem Cell Transplantation (HSCT) for Benign Indications Using Umbilical Cord Blood Units (UCB) That Were Depleted of Plasma, but Not of Red Blood Cells." Blood, 2005, vol. 106, No. 11, pp. 451B-452B.

Meyer, E.A., et al., "Cord Blood: Establishing a National Hematopoietic Stem Cell Bank Program," Institute of Medicine of the National Academies, 2005, The National Academies Press, Washington, D.C., pp. 204-205.

Hall, J.G. et al., "Unrelated Umbilical Cord Blood Transplantation for an Infant With β-Thalassemia Major," *J. Pediatr. Hematol. Oncol.*, Jun. 2004, vol. 26, No. 6, pp. 382-385.

Mao, P. et al., "Umbilical cord blood transplant for adult patients with severe aplastic anemia using anti-lymphocyte globulin and cyclophosphamide as conditioning therapy," *Bone Marrow Transplantation*, 2004, vol. 33, pp. 33-38.

Walters, M.C et al., "Sibling donor cord blood transplantation for hematological disorders," *Blood*, Nov. 16, 2003, vol. 102, No. 11, p. 762A, Abstract.

Yang, H. et al., "High-efficiency volume reduction of cord blood using pentastarch," *Bone Marrow Transplantation*, 2001, vol. 27, pp. 457-461.

Supplementary European Search Report mailed on Jul. 9, 2009, for EP Application No. 06771915.3 filed on Jun. 2, 2006, 2 pages.

Grewal, S.S. et al., "Unrelated donor hematopoietic cell transplantation: marrow or umbilical cord blood?" *Blood*, Jun. 1, 2003, vol. 101, No. 11, pp. 4233-4244.

\* cited by examiner

A

B

C

A

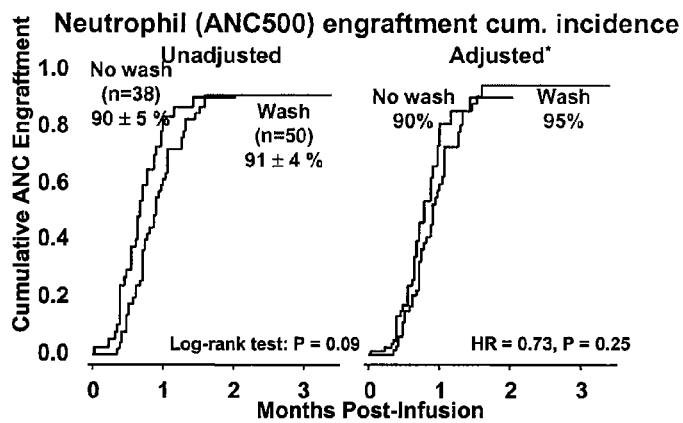

Adjusted via Cox Regression for malignancy, TNC dose, single vs. double cord TX, HLA matches, recipient sex, age and high risk status. (There were a total of 88 cases with complete records – started with all 118 patients.)

B

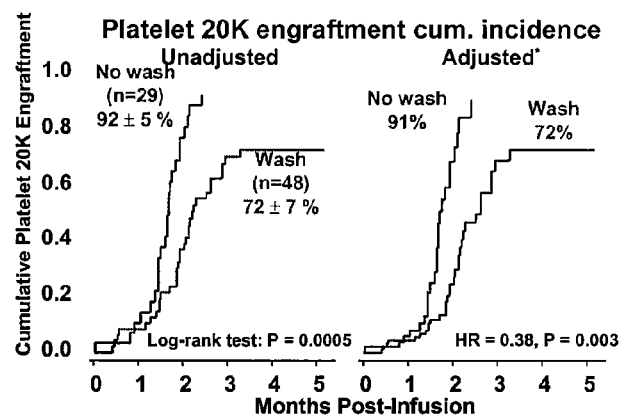

Adjusted via Cox Regression for malignancy, TNC dose, single vs. double cord TX, HLA matches, recipient sex, age and high risk status. (There were a total of 77 cases with complete records – started with all 118 patients.)

C

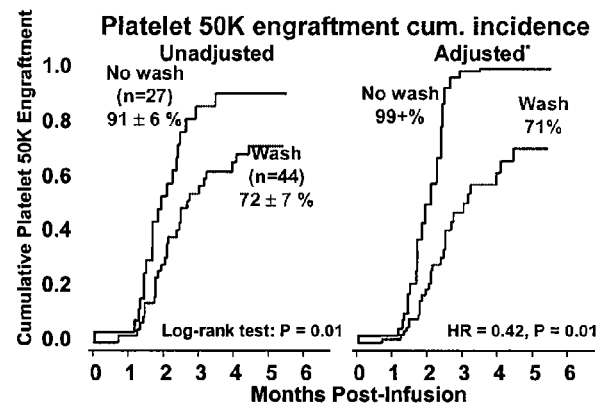

Adjusted via Cox Regression for malignancy, TNC dose, single vs. double cord TX, HLA matches, recipient sex, age and high risk status. (There were a total of 71 cases with complete records – started with all 118 patients.)

*FIG. 6*

PLASMA-DEPLETED, NOT ERYTHROCYTE-DEPLETED, CORD BLOOD COMPOSITIONS AND METHOD OF MAKING

CROSS-REFERENCES TO RELATED APPLICATIONS

The present application claims the benefit of U.S. Provisional Application Nos. 60/687,127, filed Jun. 2, 2005, and 60/733,956, filed Nov. 3, 2005, the disclosures of which are herein incorporated by reference in their entirety for all purposes.

BACKGROUND OF THE INVENTION

There is considerable interest in the identification, isolation and generation of human stem cells. Human stem cells are totipotential or pluripotential precursor cells capable of self renewal and generating a variety of mature human cell lineages. This ability serves as the basis for the cellular differentiation and specialization necessary for organ and tissue development. Recent success at transplanting stem cells have provided new clinical tools to reconstitute and/or supplement bone marrow after myeloablation due to disease, exposure to toxic chemicals, and/or radiation. Further evidence exists that demonstrates that stem cells can be employed to repopulate many, if not all, tissues and restore physiologic and anatomic functionality.

Many different types of mammalian stem cells have been characterized. For example, embryonic stem cells, embryonic germ cells, adult stem cells, and other committed stem cells or progenitor cells are known. In fact, certain stem cells have not only been isolated and characterized, but have also been cultured under conditions to allow a limited degree of differentiation. Because of the tens of millions of possible combinations of HLA types in the population, a basic problem remains, in that it is very difficult to obtain sufficient quantities, populations, and varieties of HLA types of human stem cells which are capable of differentiating into all cell types that can be HLA matched to individual patients. Stem cells of different HLA types are in critically short supply. Due to their importance in the treatment of a wide variety of disorders, including malignancies, inborn errors of metabolism, hemoglobinopathies, and immunodeficiencies, it would be highly advantageous to have an adequate source of stem cells of various HLA types.

Obtaining sufficient numbers of human stem cells has been problematic for several reasons. First, isolation of normally occurring populations of stem cells in adult tissues has been technically difficult and costly due, in part, to very limited quantities found in blood or tissue. Second, procurement of these cells from embryos or fetal tissue, including aborted fetuses, has raised ethical concerns. Alternative sources that do not require the use of cells procured from embryonic or fetal tissue are therefore essential for further progress in the clinical use of stem cells. There are, however, few viable alternative sources of stem cells, particularly human stem cells, and thus the supply is limited. Furthermore, harvesting of stem cells from alternative sources in adequate amounts for therapeutic and research purposes is generally laborious, involving, e.g., harvesting of cells or tissues from a donor subject or patient, culturing and/or propagation of cells in vitro, dissection, etc.

For example, U.S. Pat. No. 5,486,359 discloses human mesenchymal stem cell (HMSC) compositions derived from the bone marrow that serve as the progenitors for mesenchymal cell lineages. Homogeneous HMSC compositions are obtained by positive selection of adherent marrow or periosteal cells that are free of markers associated with either hematopoietic cells or differentiated mesenchymal cells. The isolated mesenchymal cell populations display characteristics associated with mesenchymal stem cells, have the ability to regenerate in culture without differentiating, and have the ability to differentiate into specific mesenchymal lineages when either induced in vitro or placed in vivo at the site of damaged tissue. The drawback of such methods, however, is that they first require the invasive and painful harvesting of marrow or periosteal cells from a human donor in order to subsequently isolate HMSCs.

PCT Publication No. WO 00/73421 discloses human amniotic epithelial cells derived from placenta at delivery that are isolated, cultured, cryopreserved for future use, or induced to differentiate. Amniotic epithelial cells are isolated from the amniotic membrane according to standard cell isolation techniques. These cells are multipotential and can differentiate into epithelial tissues such as corneal surface epithelium or vaginal epithelium. The drawback of such methods, however, is that they are labor-intensive and the yield of stem cells is very low. In fact, to obtain a sufficient number of stem cells for typical therapeutic or research purposes, amniotic epithelial cells must first be isolated from the amnion and then cultured and expanded in vitro.

Umbilical cord blood is a known alternative source of hematopoietic progenitor stem cells. Stem cells from cord blood are routinely cryopreserved for hematopoietic reconstitution, a therapeutic procedure used in bone marrow and other related transplantations (see, e.g., U.S. Pat. Nos. 5,004,681 and 5,192,553). Conventional techniques for the collection of cord blood are based on the use of a needle or cannula, which is used with the aid of gravity to drain cord blood from the placenta (see, e.g., U.S. Pat. Nos. 5,004,681, 5,192,553, 5,372,581, and 5,415,665). The needle or cannula is usually placed in the umbilical vein and the placenta is gently massaged to aid in draining cord blood from the placenta. A major limitation of stem cell procurement from cord blood, however, has been the frequently inadequate volume of cord blood obtained, resulting in insufficient cell numbers to effectively reconstitute bone marrow after transplantation.

Stem cells have the potential to be used in the treatment of a wide variety of diseases and disorders, including malignancies, genetic diseases, hemoglobinopathies, and immunodeficiencies. However, stem cells from umbilical cord blood are in critically short supply due to restrictions on their collection, the inadequate numbers of cells typically collected from cord blood, especially if used to treat an adult patient, and the extraordinary cost of establishing a large inventory. As such, there is a strong need in the art for cord blood compositions that contain an adequate number of hematopoietic stem cells sufficient to effectively reconstitute bone marrow after transplantation. There is also a need in the art for methods of preparing such cord blood compositions and using them for therapeutic purposes. The present invention satisfies these and other needs.

BRIEF SUMMARY OF THE INVENTION

The umbilical cord blood (UCB) compositions of the present invention possess the advantageous features of having plasma that is substantially depleted but red blood cells (RBC) that are not depleted from the UCB unit, i.e., a plasma-depleted, non-red blood cell-depleted composition. Such UCB units can be prepared by a process that combines plasma depletion with cryopreservation, selection, thawing, and/or transplantation of hematopoietic stem cells to provide superior clinical outcomes relative to whole blood or RBC-depleted UCB units by maximizing post-processing cell recovery and post-thaw infusion cell dose. Methods for treating a wide variety of malignant diseases and benign diseases associated with the hematopoietic system by administering the UCB compositions of the present invention are also provided.

In one aspect, the present invention provides an umbilical cord blood (UCB) composition comprising at least about 50% red blood cells by volume and an anticoagulant, wherein plasma is substantially depleted but red blood cells are not depleted. Preferably, the UCB composition comprises at least about 65% red blood cells by volume. In certain instances, the UCB composition comprises from about 0% to about 30% plasma by volume, preferably from about 10% to about 30% plasma by volume.

In one embodiment, the UCB composition comprises stem cells including, e.g., hematopoietic stem cells. In another embodiment, the UCB composition comprises from about 5% to about 40% by volume of anticoagulant, preferably from about 5% to about 20% by volume of anticoagulant. Generally, the anticoagulant contains citric acid, sodium citrate, sodium phosphate, dextrose, and/or adenosine. Preferably, the anticoagulant contains all of these components (i.e., CPDA).

In yet another embodiment, the UCB composition further comprises a cryoprotectant. Preferably, the UCB composition comprises from about 5% to about 15% by volume of cryoprotectant. In certain instances, the cryoprotectant is dimethyl sulfoxide (DMSO). In certain other instances, the cryoprotectant is a mixture of DMSO and Gentran® 40 (a dextran with an average molecular weight of 40,000 Daltons) or DMSO and hydroxyethyl starch (HES). In a preferred embodiment, the cryoprotectant is added as a solution until the final concentration of DMSO is from about 5% to about 10%.

In other embodiments of the present invention, the UCB composition has one or more of the following characteristics: (1) a red blood cell (RBC) concentration of at least about $0.4 \times 10^6$ RBC/µl (e.g., from about $0.4 \times 10^6$ to about $8 \times 10^6$ RBC/µl), preferably at least about $3.2 \times 10^6$ RBC/µl, more preferably at least about $3.8 \times 10^6$ RBC/µl; (2) an RBC number of from about $0.5 \times 10^9$ to about $5 \times 10^9$ RBC, preferably from about $1 \times 10^9$ to about $2.5 \times 10^9$ RBC; (3) a white blood cell (WBC) concentration of from about $3 \times 10^3$ to about $70 \times 10^3$ WBC/µl, preferably about $15 \times 10^3$ WBC/µl; (4) a WBC number of at least about $20 \times 10^7$ WBC (e.g., from about $20 \times 10^7$ to about $500 \times 10^7$ WBC), preferably at least about $90 \times 10^7$ WBC; (5) a CD34+ cell number of from about $1 \times 10^4$ to about $1 \times 10^8$ CD34+ cells, preferably from about $1 \times 10^6$ to about $5 \times 10^7$ CD34+ cells; (6) a percentage of CD34+ cells in the WBC fraction of from about 0.018% to about 4.3%, preferably from about 0.15% to about 1.8%; (7) a total nucleated cell number of from about $20 \times 10^7$ to about $500 \times 10^7$ nucleated cells, preferably from about $90 \times 10^7$ to about $300 \times 10^7$ nucleated cells; and (8) a percentage of nucleated cells in the cellular fraction of from about 0.18% to about 1.8%, preferably about 0.54%. One skilled in the art will appreciate that the CD34+ cell number will vary depending on the particular assay used. In certain instances, the UCB composition has one or more of the above-described characteristics before adding the cryoprotectant. Preferably, the UCB composition has one or more of the above-described characteristics after adding the cryoprotectant.

In another aspect, the present invention provides an umbilical cord blood (UCB) composition comprising at least about 50% red blood cells by volume, a red blood cell concentration of at least about $3.2 \times 10^6$ red blood cells/µl, and an anticoagulant, wherein plasma is substantially depleted but red blood cells are not depleted. Preferably, the UCB composition comprises at least about 65% red blood cells by volume. In certain instances, the UCB composition comprises from about 0% to about 30% plasma by volume, preferably from about 10% to about 30% plasma by volume.

In one embodiment, the UCB composition comprises stem cells including, e.g., hematopoietic stem cells. In another embodiment, the UCB composition comprises from about 5% to about 40% by volume of anticoagulant, preferably from about 5% to about 20% by volume of anticoagulant. In yet another embodiment, the UCB composition further comprises a cryoprotectant. Preferably, the UCB composition comprises from about 5% to about 15% by volume of any cryoprotectant or mixtures thereof described herein (e.g., a mixture of DMSO and Gentran® 40). In other embodiments of the present invention, the UCB composition has one or more of the above-described characteristics (e.g., at least about $3.8 \times 10^6$ RBC/µl, etc.) before and/or preferably after adding the cryoprotectant.

In yet another aspect, the present invention provides a method for treating a malignant disease (e.g., hematologic malignancy) or benign disease or disorder (e.g., disease or disorder associated with the hematopoietic system) by administering to a mammalian subject (e.g., a human) an effective amount of a plasma-depleted UCB composition described herein. In certain instances, the human has a weight of greater than about 50 kg (i.e., adult patient). In certain other instances, the human has a weight of less than about 50 kg (i.e., pediatric patient).

In one embodiment, the malignant disease is a hematologic malignancy including, without limitation, acute lymphoblastic leukemia, acute myelogeneous leukemia, chronic myelogenous leukemia, myelodysplastic disorders, juvenile chronic myelogenous leukemia, and non-Hodgkin's lymphoma. In another embodiment, the benign disease or disorder is associated with the hematopoietic system including, without limitation, a hemoglobinopathy, a bone marrow failure syndrome, an immune deficiency, a metabolic/storage disease, a neutrophil disorder, a platelet disease, a viral infection such as an HIV infection, and an autoimmune disorder. Preferably, the hemoglobinopathy is thalassemia (e.g., transfusion-dependent thalassemia, thalassemia major, etc.) or sickle cell disease. Additional examples of malignant diseases and benign disorders associated with the hematopoietic system suitable for prevention or treatment with the plasma-depleted cord blood compositions of the present invention are described below.

In other embodiments of the present invention, the plasma-depleted UCB composition that is administered to the mammalian subject for the treatment or curative transplantation of hematopoietic diseases provides one or more of the following superior clinical outcomes: (1) an increase in the cumulative incidence of neutrophil engraftment relative to whole cord blood or red blood cell-depleted cord blood; (2) an increase in the cumulative incidence of platelet engraftment relative to whole cord blood or red blood cell-depleted cord blood; (3) an increase in the speed to neutrophil engraftment relative to whole cord blood or red blood cell-depleted cord blood; (4) an increase in the speed to platelet engraftment relative to whole cord blood or red blood cell-depleted cord blood; (5) an increase in the disease free survival rate relative to whole cord blood, red blood cell-depleted cord blood, bone marrow, or peripheral blood stem cells; (6) a decrease in the transplant related mortality rate relative to whole cord blood, red blood cell-depleted cord blood, bone marrow, or peripheral blood stem cells; (7) an increase in the overall survival rate relative to whole cord blood, red blood cell-depleted cord blood, bone marrow, or peripheral blood stem cells; and (8) a decrease in the incidence of acute and chronic graft versus host disease relative to bone marrow or peripheral blood stem cells. As used herein, an increase or decrease in one of the above-described clinical outcomes refers to a difference of at least about 1%, 5%, 10%, 15%, 20%, 25%, 30%, 35%, 40%, 45%, or 50%, relative to whole cord blood, red blood cell-depleted cord blood, bone marrow, and/or peripheral blood stem cells. Preferably, the plasma-depleted UCB composition that is administered to the mammalian subject provides at least one, two, three, four, five, six, or more of the above-described clinical outcomes.

In another embodiment, the plasma-depleted UCB composition is administered as a multiple dose to the mammalian subject. For example, the multiple dose can be a double cord blood unit dose, a triple cord blood unit dose, etc. Preferably, the multiple dose decreases the relapse rate in said mammalian subject relative to a single dose. In yet another embodiment, the plasma-depleted cord blood composition is administered in combination with HLA matched, mismatched, or haploidentical bone marrow, peripheral blood stem cells, or mesenchymal stem cells.

The plasma-depleted cord blood composition can either be washed or not washed between thawing and administering to the mammalian subject. Preferably, the composition is not washed. However, one skilled in the art will appreciate that the composition may be washed if the mammalian subject has impaired kidney function or a low body weight. In certain instances, the composition is diluted between thawing and administering to the mammalian subject. Preferably, the composition is administered by infusion into the mammalian subject.

In still yet another aspect, the present invention provides a method for preparing a plasma-depleted umbilical cord blood (UCB) composition by removing a volume of plasma from a UCB sample containing an anticoagulant.

The UCB sample is typically collected from a donor such as a newborn and/or the newborn's mother. In one embodiment, the plasma-depleted cord blood composition comprises from about 5% to about 40% by volume of anticoagulant, preferably from about 5% to about 20% by volume of anticoagulant. Generally, the anticoagulant contains citric acid, sodium citrate, sodium phosphate, dextrose, and/or adenosine. Preferably, the anticoagulant contains all of these components (i.e., CPDA).

In another embodiment, the method further comprises the step of adding a cryoprotectant. Preferably, the plasma-depleted cord blood composition comprises from about 5% to about 15% by volume of cryoprotectant. In certain instances, the cryoprotectant is dimethyl sulfoxide (DMSO). In certain other instances, the cryoprotectant is a mixture of DMSO and Gentran® 40 or DMSO and hydroxyethyl starch (HES). In a preferred embodiment, the cryoprotectant is added as a solution until the final concentration of DMSO is from about 5% to about 10%.

In yet another embodiment, the method further comprises the step of freezing the plasma-depleted cord blood composition containing cryoprotectant at a rate of about −1° C. per minute from about 4° C. to about −50° C., and thereafter at a rate of about −1° C. per minute from about −50° C. to about −90° C. The method can further comprise the step of storing the frozen composition at a temperature of below about −135° C., preferably below about −150° C. The method can further comprising the step of thawing the frozen composition and either washing or not washing the thawed composition before administering to a mammalian subject. In certain instances, the method further comprises ex vivo expanding the population of stem cells either before or after cryopreservation. In certain other instances, the method further comprises determining whether the plasma-depleted cord blood composition meets certain selection criteria before proceeding with subsequent steps, e.g., administering to a mammalian subject.

In a further aspect, the present invention provides a method for collecting viable stem cells, e.g., hematopoetic stem cells, by first collecting a stem cell source from a donor. After mixing the stem cell source with an anticoagulant, the volume of the stem cell source is reduced by centrifugation at a temperature between about 15° C. and about 26° C. Liquid, e.g., plasma, is removed from the stem cell source after centrifugation, leaving a concentrated stem cell source with a reduced volume. The concentrated stem cell source is transferred to a freezing container and cooled to between about 2° C. and about 8° C. for about 30 to about 60 minutes. A cryoprotectant solution including a mixture of a 1:1 (volume/volume) solution of about 50% DMSO and a low molecular weight polysaccharide is made and kept between about 2° C. and about 8° C. The cryoprotectant solution is added to the concentrated stem cell source in the freezing container. While the cryoprotectant is added, the concentrated stem cell source in the freezing container is moved to achieve mixing as soon as the cryoprotectant solution is added. The motion is provided by placing the concentrated stem cell source in the freezing container on, for example, a rocking platform. The freezing container containing the concentrated stem cell source is maintained at a temperature of between about 2° C. and about 8° C. The cryoprotectant is preferably added using a programmable syringe pump. A cryoprotectant-stem cell mixture is thus formed with a DMSO concentration between about 5% and about 15% by volume, preferably between about 5% and about 10%.

In certain instances, the collected viable stem cells are stored. As a non-limiting example, the cryoprotectant-stem cell mixture in the freezing container as prepared according to the above-described method can be placed in an aluminum storage cassette that has been pre-cooled to between about 2° C. and about 8° C. The aluminum storage cassette can then be placed in a controlled rate freezer and frozen at a controlled rate. Typically, this should occur within about 10 minutes of receiving the freezing container. After freezing, the frozen freezing container with the frozen cryoprotectant-stem cell mixture can be transferred from the controlled rate freezer to a liquid nitrogen tank for storage of viable stem cells.

Suitable stem cell sources include, but are not limited to, adult stem cell sources, fetal stem cell sources, embryonic stem cell sources, placental blood, umbilical cord blood, peripheral blood, bone marrow, and fetal liver. In certain instances, the stem cell source is placental blood and/or umbilical cord blood. In some embodiments, the stem cell source comprises nucleated cells and more than about 95% of the nucleated cells are present in the concentrated stem cell source.

In other embodiments, the anticoagulant comprises citrate, phosphate, and dextrose (CPD). In a further embodiment, the temperature of the freezing container containing the concentrated stem cell source is maintained at a temperature of between about 2° C. to about 8° C. during cryoprotectant addition, e.g., by wrapping the bag in ice packs. In certain instances, the cryoprotectant-stem cell mixture is split between at least two freezing containers before freezing.

The stem cell source-anticoagulant mixture is typically stored at a temperature between about 15° C. and about 26° C. The stem cell source-anticoagulant mixture can be stored in this manner for up to about 48 hours before its volume is reduced. In another embodiment, the cryoprotectant solution is cooled to between about 2° C. and about 8° C. In certain instances, the low molecular polysaccharide solution comprises dextran. In yet another embodiment, the transfer from the controlled rate freezer to the liquid nitrogen tank is accomplished within about 10 minutes. In certain instances, the transfer from the controlled rate freezer to the liquid nitrogen tank is accomplished within about 10 seconds.

In a further embodiment, the cryoprotectant-stem cell mixture includes nucleated cells and at least about 80%, 85%, 90%, or 95% of the nucleated cells are viable after thawing.

Other features, objects, and advantages of the present invention and its preferred embodiments will become apparent from the detailed description, examples, and claims that follow.

BRIEF DESCRIPTION OF THE DRAWINGS

FIG. 1A shows the ANC500 engraftment unadjusted cumulative incidence for all patients (n=106); FIG. 1B shows the platelet 20K engraftment unadjusted cumulative incidence for all patients (n=89); FIG. 1C shows the $1^{st}$ year patient survival rate for all patients (n=118); and FIG. 1D shows the $1^{st}$ year relapse-free survival rate for all malignant patients (n=85).

FIG. 2A shows the ANC500 engraftment unadjusted cumulative incidence for remission/$1^{st}$ transplant patients (n=87); FIG. 2B shows the platelet 20K engraftment unadjusted cumulative incidence for remission/$1^{st}$ transplant patients (n=72); FIG. 2C shows the $1^{st}$ year patient survival rate for remission/$1^{st}$ transplant patients (n=98); and FIG. 2D shows the $1^{st}$ Yr relapse-free survival rate for remission/$1^{st}$ transplant malignant patients (n=67).

FIG. 3A shows the neutrophil (ANC500) engraftment cumulative incidence; FIG. 3B shows the platelet 20K engraftment cumulative incidence; FIG. 3C shows the relapse rate; and FIG. 3D shows the patient mortality and overall survival rates.

FIG. 4A shows the neutrophil (ANC500) engraftment cumulative incidence; FIG. 4B shows the platelet 20K engraftment cumulative incidence; FIG. 4C shows the relapse rate; and FIG. 4D shows the patient mortality and overall survival rates.

FIG. 5A shows the ANC500 engraftment unadjusted cumulative incidence for remission/$1^{st}$ transplant patients, (n=87); FIG. 5B shows the platelet 20K engraftment cumulative incidence for remission/$1^{st}$ transplant patients (n=72); and FIG. 5C shows the patient overall survival for remission/$1^{st}$ transplant patients (n=98).

FIG. 6 shows a comparison between patients receiving washed or non-washed cord blood units. FIG. 6A shows the neutrophil (ANC500) engraftment cumulative incidence; FIG. 6B shows the platelet 20K engraftment cumulative incidence; and FIG. 6C shows the platelet 50K engraftment cumulative incidence.

DETAILED DESCRIPTION OF THE INVENTION

I. Definitions

Figure 1:
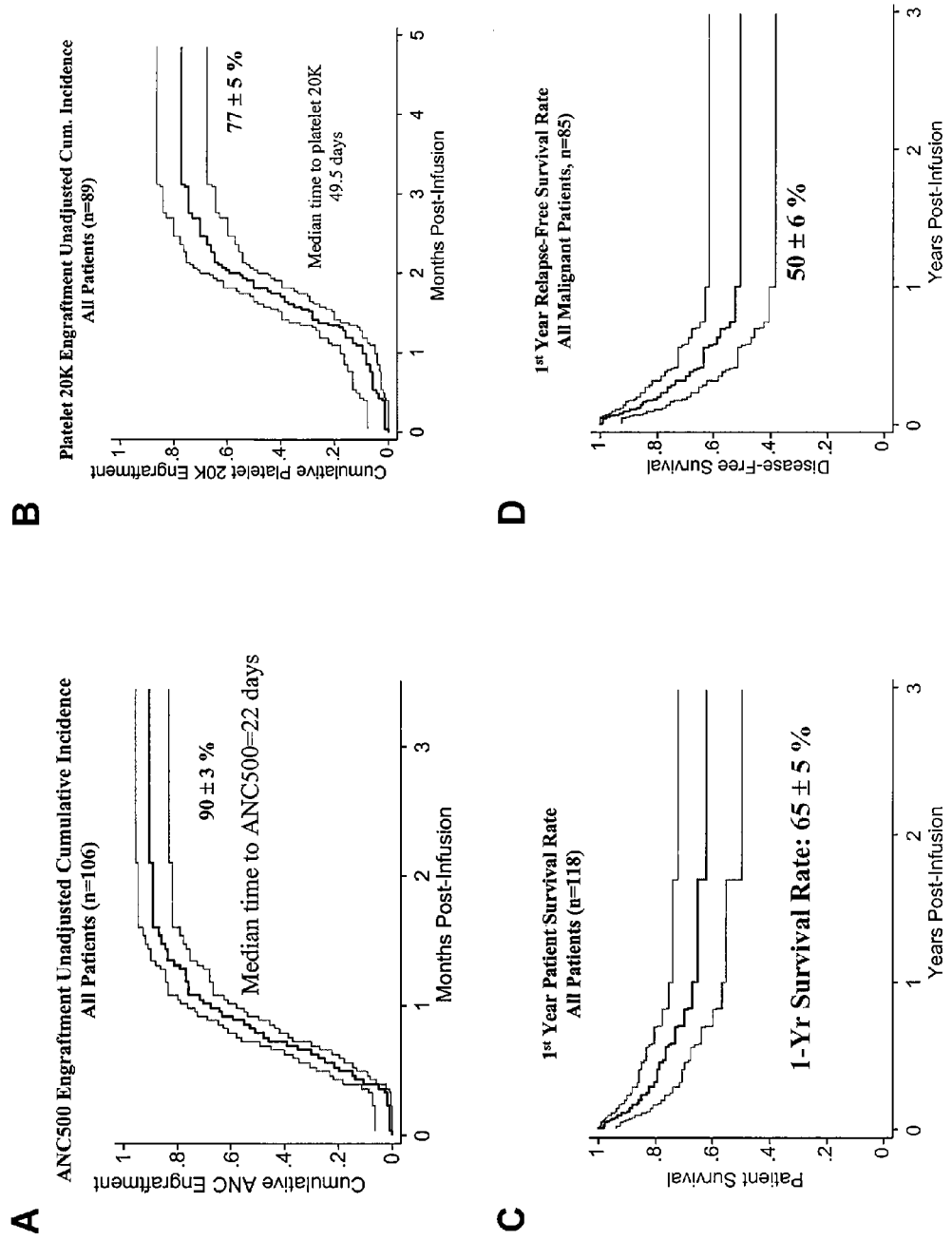
FIG. 1 shows the overall results for all patients.

As used herein, the following terms have the meanings ascribed to them unless specified otherwise.

The term "stem cell" refers to any cell that has the ability to divide for indefinite periods of time and to give rise to specialized cells. Stem cells emanate from all germinal layers (i.e., ectoderm, mesoderm, and endoderm). Typical sources of stem cells include embryos, bone marrow, peripheral blood, umbilical cord blood, placental blood, and adipose tissue. Stem cells can be pluripotent, meaning that they are capable of generating most tissues on an organism. For example, pluripotent stem cells can give arise to cells of the skin, liver, blood, muscle, bone, etc. In contrast, multipotent or adult stem cells typically give rise to limited types of cells. For example, hematopoietic stem cells typically give rise to cells of the lymphoid, myeloid, and erythroid lineages. Viable cells are cells that are alive and frequently are capable of growth and division. Those of skill in the art are aware of methods to determine the viability of cells, e.g., by the ability to exclude trypan blue dye. The term stem cell as used herein includes progenitor cells unless otherwise noted.

"Nucleated cells" refers to cells that have a nucleus, i.e., an organelle that comprises chromosomal DNA. Nucleated cells include, e.g., white blood cells and stem cells. "Unnucleated cells" includes, e.g., adult red blood cells.

As used herein, the terms "plasma is substantially depleted" and "plasma-depleted" refer to the umbilical cord blood compositions of the present invention in which a volume of plasma greater than about 40%, 45%, 50%, 55%, 60%, 65%, 70%, 75%, 80%, 85%, 90%, or 95% has been removed. In a preferred embodiment, plasma is substantially depleted by centrifuging an umbilical cord blood-anticoagulant mixture and separating the cellular fraction from the plasma fraction. The plasma volume remaining following substantial depletion is typically from about 0% to about 30% by volume, preferably from about 10% to about 30% by volume.

The terms "non-red blood cell depleted" and "red blood cells are not depleted" as used herein refer to the umbilical cord blood compositions of the present invention in which a volume of red blood cells less than about 30%, 25%, 20%, 15%, 10%, 5%, 4%, 3%, 2%, or 1% has been removed. Although the present invention does not include a step of removing red blood cells from the umbilical cord blood unit, one skilled in the art will understand that the step of depleting the unit of plasma and/or any other processing steps may remove a small volume of red blood cells.

The term "speed to neutrophil engraftment" refers to an indication of how fast the new immune system created by the newly engrafted bone marrow is functioning and is typically indicated by the sum of the number of bands and neutrophils per volume of blood in the recipient. Preferably, the patient is immunocompromised prior to neutrophil engraftment. The shorter the speed or time to neutrophil engraftment, the more advantageous it is for the patient. Similarly, the term "speed of platelet engraftment" refers to an indication of how fast the newly engrafted bone marrow is functioning in turning out platelets which are important for clotting. Before platelet engraftment, patients are dependent on transfusion of donor platelets so that they do not have any bleeding problems. The shorter the speed or time to platelet engraftment, the more advantageous it is for the patient.

The term "cumulative incidence of engraftment" refers to the percentage of transplants that eventually show robust production of that particular hematopoietic cell lineage, e.g., neutrophils or platelets.

The terms "umbilical cord blood unit" and "UCB unit" as used herein refer to a volume of cord blood that is collected from a single donor. The UCB compositions of the present invention typically contain one UCB unit, but may also contain multiple UCB units, e.g., double cord blood units that can be administered to a patient in order to further increase cell dosage.

As used herein, the term "cryoprotectant" refers to an agent used to enhance the viability of cells while frozen. Cryoprotectants include, but are not limited to, dimethyl sulfoxide (DMSO), glycerol, ethylene glycol, propylene glycol, formamide, and hydroxyethyl starch (HES). Preferably, a low molecular weight polysaccharide such as dextran (e.g., Gentran® 40) is added to the cryoprotectant mixture. In a preferred embodiment, the cryoprotectant solution comprises about a 10:1 ratio (volume/volume) of DMSO to Gentran® 40 such as, e.g., 50% DMSO to 5% Gentran® 40, which is added to the umbilical cord blood and anticoagulant mixture to provide a final concentration of from about 5% to about 10% DMSO.

An "effective amount" of a plasma-depleted cord blood composition of the present invention is an amount sufficient to produce the desired effect, e.g., prevention or treatment of a malignant disease or a benign disease associated with the hematopoietic system.

As used herein, the term "administering" refers to the delivery of the plasma-depleted cord blood compositions of the present invention by any route including, without limitation, oral, intranasal, intravenous, intraosseous, intraperitoneal, intramuscular, intra-articular, intraventricular, intracranial, intralesional, intratracheal, intrathecal, subcutaneous, intradermal, transdermal, or transmucosal administration. Preferably, patients are infused with one, two, three, or more umbilical cord blood units prepared according to the methods of the present invention. Multiple units such as double cord blood units can be administered simultaneously or consecutively (e.g., over the course of several minutes, hours, or days) to a patient. In certain instances, the plasma-depleted cord blood units of the present invention are administered after either myeloablative, reduced intensity, or non-myeloablative therapy to eliminate the diseased bone marrow or after radiation therapy, chemotherapy, or other radiation exposure has ablated the host bone marrow. In certain other instances, the plasma-depleted cord blood units of the present invention are co-administered either simultaneously or consecutively with bone marrow and/or peripheral blood cells as combination therapy.

II. General Overview

Unlike other sources of hematopoietic stem cells, umbilical cord blood offers a supply of stem cells that is limited to the total number of cells present for that collection. In contrast, bone marrow and peripheral blood offer an almost unlimited supply of hematopoietic stem cells. Because of this inherent limitation, the total nucleated cell dosage of a given unit of umbilical cord blood is one of the most important determinants for clinical outcome, e.g., neutrophil engraftment, platelet engraftment, and the establishment of a new bone marrow. Since lack of white blood cell engraftment means lack of a functional immune system, the impact on engraftment, in turn, affects patient survival. Upon failure of engraftment, a patient will eventually succumb to infection unless the patient recovers his or her own autologous bone marrow, is rescued with his or her own stored marrow or peripheral blood stem cells, or undergoes another related or unrelated stem cell transplantation.

In the beginning of umbilical cord blood transplantation between 1988 and 1994, umbilical cord blood units were cryopreserved and banked as whole blood units, without any volume reduction. For example, 2,257 units were banked as whole blood units between 1993 and 1994 at the New York Blood Center (NYBC). As a result, cord blood transplants performed at that time used whole blood units. In fact, as of 2003, the NYBC transplanted 460 such whole blood units, representing the highest utilization rate for the different types of units that were stored.

Due to the extraordinary cost of storage space, the NYBC Cord Blood Bank developed a method to reduce the frozen volume of whole blood units in 1994, adding Hespan (hetastarch or hydroxyethyl starch) followed by centrifugation to remove excess red blood cells and plasma in order to achieve a final volume of approximately 20 ml. Another popular technique involves the purification of mononuclear cells by removing red blood cells and neutrophils using Ficoll-sedimentation gradient centrifugation. However, these techniques do not provide an adequate recovery of hematopoietic stem cells because significant numbers of such cells are trapped within the red blood cell mass and are removed along with the red blood cells. In fact, the typical hematopoietic stem cell recovery after processing is 70-75% for Hespan method and only 25-50% for the Ficoll method.

The present invention is based, in part, on the surprising discovery that processing umbilical cord blood units according to the methods described herein minimizes the degree of nucleated cell loss that severely limits the applicability of techniques such as the Hespan and Ficoll methods described above. In fact, the methods of the present invention provide umbilical cord blood compositions that contain a higher number of viable stem cells after processing, cryopreservation, and thawing, resulting in a higher average cell dosage for infusion into a patient and the surprising discovery that a significantly improved clinical outcome is achieved with plasma-depleted cord blood units when compared to red blood cell-depleted or whole blood units. The present invention is also based on the surprising discovery that not subjecting the thawed umbilical cord blood compositions of the present invention to a wash step prior to patient administration results in a higher cumulative incidence of engraftment as well as a faster speed to engraftment for both neutrophils and platelets. As such, the methods of processing umbilical cord blood units described herein and the resulting plasma-depleted, non-red blood cell-depleted compositions provide a superior rate of engraftment and a higher survival rate as compared to those umbilical cord blood products obtained from other public cord blood banks.

III. Plasma-Depletion Processing of Umbilical Cord Blood

The umbilical cord blood (UCB) compositions of the present invention possess the unique features of having plasma that is substantially depleted from the UCB unit and red blood cells (RBC) that are not depleted from the UCB unit. Such UCB units can be prepared by a process that combines plasma depletion with cryopreservation, selection, thawing, and/or transplantation of hematopoietic stem cells to provide superior clinical outcome by maximizing post-processing cell recovery and post-thaw infusion cell dose. Methods for treating a wide variety of malignant diseases (e.g., hematologic malignancies) and benign diseases associated with the hematopoietic system by administering the UCB compositions of the present invention are also provided.

In one aspect, the plasma-depleted, non-RBC-depleted UCB units are prepared by the process described below.

A newborn's UCB is collected into a collection vessel such as a multi-bag blood collection bag containing an anticoagulant. The collection vessel typically contains from about 0.1 to about 100 ml of anticoagulant (e.g., about 1, 5, 10, 15, 20, 25, 30, 35, 40, 45, 50, 55, 60, 65, 70, 75, 80, 85, 90, 95, or 100 ml). Preferably, the collection vessel contains from about 23 ml to about 35 ml of anticoagulant. Non-limiting examples of anticoagulants include a citrate, phosphate, dextrose, and adenosine mixture (CPDA), a citrate, phosphate, and dextrose mixture (CPD), and an acid, citrate, and dextrose mixture (ACD). Preferably, the anticoagulant is CPDA, which can comprise 0.299% anhydrous citric acid, 0.263% dehydrate sodium citrate, 0.222% monobasic sodium phosphate (monohydrate), 3.19% dextrose, and 0.0275% adenosine. CPDA is isotonic and has a neutral pH, so the ratio of anticoagulant to blood is not critical. However, one skilled in the art will appreciate that the composition and/or volume of the anticoagulant in the collection vessel can depend upon the volume of cord blood collected from the donor.

The collected UCB is delivered to a UCB processing laboratory, preferably within about 43 hours to allow for cryopreservation by about 48 hours after birth. However, cryopreservation up to about 72 hours after birth can also yield acceptable results.

The collection bag is weighed to determine the UCB collection volume by subtracting the collection bag weight with anticoagulant from the combined weight. The volume in the bag is determined by the volume of the UCB plus the volume of the anticoagulant.

The whole cord blood is assayed at this point to determine the complete blood count. The pre-processing hematocrit (i.e., the percentage of red blood cells by volume) with anticoagulant typically has a range of from about 20% to about 60% for over 95% of the samples. The red blood cell concentration is usually between about 2 to about $10 \times 10^6/\mu l$ and the white blood cell concentration is usually between about 1 to about $30 \times 10^6/ml$.

The UCB unit is centrifuged, e.g., in a 3-bag collection blood bag, to separate the cellular fraction from the upper plasma fraction.

The upper plasma portion is removed into the second bag, which is then sealed off. In certain instances, if the remaining mostly cellular portion contains more than 60 cc, the product can be divided into two portions (e.g., in the original bag and in the third bag), each in its own collection/transfer bag. After plasma depletion, both the hematocrit (HCT) and the RBC concentration of the UCB unit increase about 1.2 to about 3 fold (average=about 1.6 to about 1.8 fold; median=about 1.7 to about 1.8-fold) relative to whole blood or red blood cell-depleted units (see, Table 1).

TABLE 1

Comparison of blood counts of plasma-depleted, whole blood, and red blood cell-depleted cord blood units containing anticoagulant, but not cryoprotectant.

| | HCT (%) | RBC ($\times 10^6/\mu l$) | WBC ($\times 10^3/\mu l$) | Total Nucleated Cell Count ($\times 10^7/\mu l$) | % CD34+ Cells (Pro-Count Method) | Total CD34+ Cell # |
|---|---|---|---|---|---|---|
| Processed plasma-depleted samples | | | | | | |
| Average/Median | 65/66 | 5.7/5.8 | 19/18 | 96/87 (60 ml) | 0.43%/0.38% TW 0.56%/0.50% US | TW $2.4 \times 10^6$; US $3.5 \times 10^6$/ TW $1.8 \times 10^6$; US $2.7 \times 10^6$ |
| Whole blood samples | | | | | | |
| Average/Median | 40/40 | 3.5/3.4 | 10/9.6 | 96/87 (60 ml) | 0.24%/0.21% TW 0.31%/0.28% US | TW $2.4 \times 10^6$; US $3.5 \times 10^6$/ TW $1.8 \times 10^6$; US $2.7 \times 10^6$ |
| Processed RBC-depleted samples | | | | | | |
| Average/Median | 40/40 | 3.5/3.4 | 30/28 | 72/65 (60 ml) | 0.72%/0.63% TW 0.93%/0.84% US | TW $1.8 \times 10^6$; US $2.6 \times 10^6$/ TW $1.4 \times 10^6$; US $2.0 \times 10^6$ |

TW = samples from Taiwan;
US = samples from the United States.
Processed plasma-depleted samples are based on 99% recovery of red blood cells, white blood cells, and CD34+ cells, since less than about 0.1% are found in the plasma fraction. Processed RBC-depleted samples are based on 20% yield of red blood cells of original whole blood and a similar red blood cell concentration as whole blood after red cell depletion. Processed RBC-depleted samples are also based on average recovery of 75% of white blood cells and CD34+ cells and on average 75% volume reduction.

The product in each collection/transfer bag is then transferred via a sterile docking device to one freezing bag (e.g., CryoCyte® bag). Typically, the UCB units are cryopreserved in one freezing bag after plasma depletion and addition of pre-cooled (i.e., about 4° C.) cryoprotectant, e.g., with an approximate maximum volume of about 75 cc. However, some UCB units are divided into two bags, e.g., with an approximate combined maximum volume of about 150 cc.

The plasma-depleted UCB/anticoagulant mixture is then cooled to about 4° C. prior to the addition of one or more cryoprotectants. Typically, a cryoprotectant in the form of a solution is added in an amount equal to about 25% to about 50% of the UCB/anticoagulant volume. For example, in instances where the UCB/anticoagulant volume in the plasma-depleted sample is 60 ml, the volume of cryoprotectant solution can be 15 ml. As a result, the UCB unit generally comprises about 5% to about 15% by volume of the cryoprotectant, e.g., about 5%, 6%, 7%, 8%, 9%, 10%, 11%, 12%, 13%, 14%, or 15% by volume of the cryoprotectant. In a preferred embodiment, the cryoprotectant solution comprises a mixture of about 50% DMSO and about 5% Gentran® 40 (i.e., about a 10:1 ratio of DMSO to Gentran® 40), to provide a final DMSO concentration of about 5% to about 10%. The DMSO/Gentran® 40 cryoprotectant solution can be added to the UCB/anticoagulant mixture at a rate of about 0.75 ml per minute by a syringe pump with the freezing bag between ice packs on a rotator to achieve a final DMSO concentration of about 5% to about 10%. As shown in Table 2, the plasma-depleted UCB units containing both anticoagulant and cryoprotectant have a higher hematocrit (HCT) and the RBC concentration (i.e., at least about 1.6 fold) relative to whole blood or red blood cell-depleted units.

TABLE 2

Comparison of blood counts of plasma-depleted, whole blood, and red blood cell-depleted cord blood units containing anticoagulant and cryoprotectant (25% by volume DMSO).

| | HCT (%) | RBC ($\times 10^6/\mu l$) | WBC ($\times 10^3/\mu l$) | Total Nucleated Cell Count ($\times 10^7/\mu l$) | % CD34+ Cells (Pro-Count Method) | Total CD34+ Cell # |
|---|---|---|---|---|---|---|
| Processed plasma-depleted samples | | | | | | |
| Average/Median | 52/53 | 4.6/4.7 | 15/14 | 96/87 (60 ml) | 0.34%/0.30% TW 0.45%/0.40% US | TW $2.4 \times 10^6$; US $3.5 \times 10^6$/ TW $1.8 \times 10^6$; US $2.7 \times 10^6$ |
| Whole blood samples | | | | | | |
| Average/Median | 32/32 | 2.8/2.8 | 8/8 | 96/87 (60 ml) | 0.19%/0.168% TW 0.248%/0.22% US | TW $2.4 \times 10^6$; US $3.5 \times 10^6$/ TW $1.8 \times 10^6$; US $2.7 \times 10^6$ |
| Processed RBC-depleted samples | | | | | | |
| Average/Median | 32/32 | 2.8/2.8 | 24/22 | 72/65 (60 ml) | 0.58%/0.50% TW 0.74%/0.67% US | TW $1.8 \times 10^6$; US $2.6 \times 10^6$/ TW $1.4 \times 10^6$; US $2.0 \times 10^6$ |

TW = samples from Taiwan;
US = samples from the United States.
Processed plasma-depleted samples are based on 99% recovery of red blood cells, white blood cells, and CD34+ cells, since less than about 0.1% are found in the plasma fraction. Processed RBC-depleted samples are based on 20% yield of red blood cells of original whole blood and a similar red blood cell concentration as whole blood after red cell depletion. Processed RBC-depleted samples are also based on average recovery of 75% of white blood cells and CD34+ cells and on average 75% volume reduction.

The post-processing hematocrit of the plasma-depleted UCB/anticoagulant mixture in the absence of cryoprotectant is typically in the range of from about 20% to about 100%, preferably between about 40% to about 100%, and more preferably between about 50% to about 100%, e.g., at least about 50%, 55%, 60%, 65%, 70%, 75%, 80%, 85%, 90%, or 95%. As such, in preferred embodiments, the processed UCB units of the present invention have a hematocrit that is higher than the hematocrit for both whole blood UCB units (i.e., 40%) and hydroxyethyl starch (HES) red cell-depleted UCB units (i.e., 40%) (see, Table 1).

The post-processing hematocrit of the plasma-depleted UCB/anticoagulant mixture with cryoprotectant is typically in the range of from about 16% to about 80%, preferably between about 32% to about 80%, more preferably between about 40% to about 80%, and most preferably between about 50% to about 80%, e.g., about 50%, 55%, 60%, 65%, 70%, 75%, and 80%. As such, in preferred embodiments, the processed UCB units of the present invention with cryoprotectant have a hematocrit that is higher than the hematocrit for both whole blood UCB units (i.e., 32%) and HES red cell-depleted UCB units (i.e., 32%) (see, Table 2).

The post-processing red blood cell concentration for the plasma-depleted UCB/anticoagulant mixture in the absence of cryoprotectant is typically in the range of from about 0.5 to about $10 \times 10^6$ $\mu l$, preferably between about 3 to about $10 \times 10^6/\mu l$, and more preferably between about 4 to about $10 \times 10^6/\mu l$, e.g., about 4, 4.5, 5, 5.5, 6, 6.5, 7, 7.5, 8, 8.5, 9, 9.5, or $10 \times 10^6$ $\mu l$. As such, in preferred embodiments, the processed UCB units of the present invention have a red blood cell concentration that is higher than the red blood cell concentration for both whole blood UCB units (i.e., $3.5 \times 10^6/\mu l$) and HES red cell-depleted UCB units (i.e., $3.5 \times 10^6$ $\mu l$) (see, Table 1).

The post-processing red blood cell concentration for the plasma-depleted UCB/anticoagulant mixture with cryoprotectant is typically in the range of from about 0.4 to about $8 \times 10^6$ $\mu l$, preferably between about 2.4 to about $8 \times 10^6/\mu l$, and more preferably between about 3.2 to about $8 \times 10^6/\mu l$, e.g., about 3.5, 4, 4.5, 5, 5.5, 6, 6.5, 7, 7.5 or $8 \times 10^6/\mu$. As such, in preferred embodiments, the processed UCB units of the present invention with cryoprotectant have a red blood cell concentration that is higher than the red blood cell concentration for both whole blood UCB units (i.e., $2.8 \times 10^6/\mu l$) and HES red cell-depleted UCB units (i.e., $2.8 \times 10^6/\mu l$) (see, Table 2).

The post-processing white blood cell concentration for the plasma-depleted UCB/anticoagulant mixture in the absence of cryoprotectant is typically between about 3 to about $90 \times 10^6$/ml, e.g., about 5, 10, 15, 20, 25, 30, 35, 40, 45, 50, 55, 60, 65, 70, 75, 80, 85, or $90 \times 10^6$/ml. Preferably, the white blood cell concentration after processing and addition of cryoprotectant is greater than about $10 \times 10^6$/ml, e.g., about 10, 15 20, 25, 30, 35, 40, 45, or $50 \times 10^6$/ml, in a freezing volume of about 75 cc for a one bag UCB product.

In a preferred embodiment, the cellular concentration of the plasma-depleted UCB units of the present invention is at least about 25% higher than whole blood units, e.g., at least about 25%, 30%, 35%, 40%, 45%, 50%, 55%, 60%, 65%, 70%, 75%, 80%, 85%, 90%, 95%, 100%, or more.

The above-described processing of UCB units is responsible, in part, for the differences between plasma depletion and whole blood or red blood cell depletion. Advantageously, the processed UCB units of the present invention have a lower plasma volume, which produces a higher cellular concentration and a higher hematocrit. Without being bound to any particular theory, one or more of these properties provides enhanced cryopreservation with improved clinical results as compared to whole blood or red blood cell-depleted units. As a non-limiting example, the plasma-depleted UCB units of the present invention provide improved clinical results as compared to whole blood results from the New York Blood Center (NYBC).

The process of plasma depletion described herein also has the following advantages over HES or other methods of red cell depletion of UCB units: (1) lower nucleated cell loss; (2) lower CD34+ cell loss; (3) lower colony forming unit loss; (4) a substantially higher hematocrit; and (5) a higher cellular concentration (i.e., including red blood cells). In addition, the presence of a larger volume allows the processed UCB units of the present invention to withstand post-thaw manipulation techniques because of the longer amount of time it takes to thaw the entire product versus a red cell depletion product with a typically smaller volume (e.g., 25 ml). As such, one or more of the above properties accounts for the superior clinical outcome observed in patients receiving a plasma-depleted UCB transplant. However, the plasma-depleted UCB units of the present invention provide improved clinical results as compared to red cell-depleted results from the New York Blood Center (NYBC), whether stored in conventional dewar liquid nitrogen tanks or the BioArchive® liquid nitrogen tanks made by ThermoGenesis Corp.

The plasma-depleted UCB mixture containing both anticoagulant and cryoprotectant is then frozen using a non-conventional programmed flatline freezing curve of about −1° C. per minute from about 4° C. to about −50° C. This freezing step can be preformed in the absence of a dip to compensate for the release of heat resulting from the phase transition (i.e., heat of fusion) of the composition from liquid to ice. After the initial freezing step, the processed UCB units are further frozen at a rate of about −10° C. per minute from about −50° C. to about −90° C. Traditional programmed freezing curves at other banks (e.g., the St. Louis Cord Blood Bank) have a dip at the temperature point expected for the heat of fusion, with the rationale of compensating for the heat of fusion that is generated. However, this compensation occasionally overcompensates and generates a steep cooling rate that at more than −5° C. per minute kills cells. For the flat freezing curve described herein, the heat of fusion causes a sharp rise in temperature that does not kill cells prior to the phase change. Additionally, the flat freezing curve of about −1° C. per minute does not produce a steep cooling rate that would kills cells. The processed UCB units are typically stored below about −135° C., and preferably below about −150° C., in liquid nitrogen (e.g., liquid and/or vapor phase).

The plasma-depleted UCB units of the present invention unexpectedly achieve a better clinical outcome than whole blood UCB units, although both contain a similar number of cells and should theoretically achieve the same recovery of cells. For example, plasma-depleted UCB units provide an improved clinical outcome when compared with NYBC historical data for whole blood UCB units. Without being bound to any particular theory, plasma-depleted UCB units are more potent, provide better preservation of stem cell viability, and/ or lack inhibitory factors in the plasma that are removed by processing to enable faster immune reconstitution in the patient and/or the red blood cells and lysed hemoglobin in a concentrated state help preserve stem cell viability. In fact, cellular concentration and potency are at least about 1.5 times that of whole blood UCB.

In a preferred embodiment, the plasma-depleted UCB units of the present invention meet the following selection criteria: (1) minimum nucleated cell number as a single or double unit combined dose of about $2.0 \times 10^7$/kg; (2) normalized CD34+ cell dose as a single or double unit combined dose of about $1.0 \times 10^5$/kg; and (3) minimum of 4/6 HLA A/B/DR matches at high resolution. CD34+ dose is usually normalized for inter-laboratory variation and is determined by taking the average CD34+ percentage for 100 cord blood units at a particular laboratory and dividing the value by 0.300% (the approximate average percentage of CD34+ cells in the U.S. general population if the Becton Dickinson Pro-Count flow cytometry enumeration method is used), in which the individual dose is multiplied by the ratio to arrive at a normalized CD34+ cell dose. One skilled in the art will readily appreciate that any or all of the above selection criteria can vary depending on the circumstances and assay methods used.

Prior to transplantation, the plasma-depleted UCB units of the present invention are thawed. The thawed units are then either washed or not washed prior to administration. Preferably, the thawed units are not washed. In certain instances, the thawed, non-washed units are administered to a patient by direct infusion. In certain other instances, the thawed, non-washed units are administered to a patient by infusion after the units have been diluted and/or reconstituted with an isotonic solution containing, for example, human serum albumin and Gentran® (Dextran). As shown in Example 4, not washing plasma-depleted UCB units after thawing improves the clinical outcome in patients transplanted with such units. In fact, the cumulative incidence to platelet engraftment and the speed to engraftment for neutrophils and platelets are both increased relative to washed units, indicating that post-thaw washing actually delays or reduces the cumulative incidence of the engraftment of hematopoetic stem cells. Additionally, not washing plasma-depleted UCB units after thawing provides better recovery of nucleated cells, thereby increasing the total nucleated cell (TNC) dosage that is administered relative to washed units.

However, in certain other instances, e.g., with small children or when patients have compromised renal function, the thawed, plasma-depleted units are administered to a patient by infusion after the units have been washed with an isotonic solution containing, for example, human serum albumin and Gentran® (Dextran).

In another embodiment, a colony forming unit (CFU) assay can be performed on the thawed, plasma-depleted cord blood present in a sealed tubing or segment attached or unattached to the freezing bag containing the bulk of the cord blood, or on the actual thawed, plasma-depleted UCB units in the freezing bag to demonstrate the replicative potential of the particular UCB unit and to withhold the unit should the CFU assay fail to show growth on repeated testing. In certain instances, the CFU assay takes into account the higher red blood cell density, higher free hemoglobin concentration, and higher red blood cell ghost concentration versus whole blood and red blood cell-depleted units. As such, a dilution of from about 1 to about 10 or from about 1 to about 20 in a solution containing human serum albumin or fetal calf serum and dextran is used immediately after thawing prior to the plating of cells on the semisolid medium for CFU growth.

Administration of the plasma-depleted UCB units of the present invention provides an unprecedented clinical outcome for unrelated UCB transplants in terms of the cumulative incidence of engraftment, engraftment speed, survival rate, disease free survival, relapse rate, and graft versus host disease rate. With regard to benign diseases associated with the hematopoietic system, the UCB units described herein provide an unprecedented clinical outcome for unrelated UCB transplants in terms of the cumulative incidence to engraftment, engraftment speed, survival rate, disease free survival, relapse rate, and graft versus host disease rate that advantageously tips the risk ratio in favor of benefit with improved survival. For example, the clinical outcome in patients transplanted with unrelated HLA-mismatched plasma-depleted UCB units for benign diseases is better than the related HLA-matched cord blood transplants previously reported using whole blood or red cell-depleted cord blood units. In fact, the clinical outcome using unrelated HLA-mismatched plasma-depleted UCB is comparable to related HLA-matched transplants using bone marrow n terms of overall survival and disease free survival, as well as speed to neutrophil engraftment for benign indications. Additionally, plasma-depleted UCB units engraft faster than the red blood cell-depleted UCB units described in Kurtzberg et al., *N. Engl. J. Med.*, 352:2069-2081 (2005), despite a larger cell dose and younger and lighter patients used in that study. With regard to malignant diseases, the UCB units described herein provide an unprecedented clinical outcome for unrelated UCB transplants in terms of the cumulative incidence to engraftment, engraftment speed, survival rate, disease free survival, relapse rate, and graft versus host disease rate.

In sum, the UCB plasma depletion processing of the present invention provides the following benefits for a given cord blood unit: (1) maximal post-processing nucleated cell recovery; (2) maximal post-processing CD34+ cell recovery; (3) maximal post-processing colony forming unit recovery; (4) maximal post-processing stem cell recovery (by extrapolation); (5) maximal post-thaw nucleated cell recovery; (6) maximal post-thaw CD34+ cell recovery; (7) maximal post-thaw colony forming unit recovery; (8) maximal post-thaw stem cell recovery (by extrapolation); (9) maximal infused nucleated cell dose; (10) maximal infused CD34+ cell dose; (11) maximal infused colony forming unit dose; and (12) maximal infused stem cell dose (by extrapolation). Additionally, by maximizing the cell dose through the processing, cryopreservation, thawing, and selection techniques described herein, the present invention improves the following clinical outcome parameters in both pediatric and adult patients transplanted with single or double plasma-depleted UCB units: (1) cumulative incidence of neutrophil engraftment; (2) cumulative incidence of immune reconstitution (by extrapolation); (3) cumulative incidence of platelet engraftment; (4) speed to neutrophil engraftment; (5) speed to immune reconstitution (by extrapolation); (6) speed to platelet engraftment; (7) disease free survival; (8) relapse rate; (9) transplant related mortality, especially death due to graft failure and infection (slow engraftment or graft failure), and (10) most importantly, overall survival.

Collection of Umbilical Cord Blood

The present invention provides umbilical cord blood compositions that have been processed to substantially remove plasma but not red blood cells. Umbilical cord blood is a rich source of stem cells and can be obtained easily and without trauma to the donor. In contrast, the collection of bone marrow cells for transplantation is a traumatic experience which is costly in terms of time and money spent for hospitalization. Preferably, umbilical cord blood is collected by direct drainage from the umbilical cord. As such, following delivery of the infant, the umbilical cord can be doubly cross-clamped and transected just above the crushed portion in the clamp, and the resulting flow of fetal blood from umbilical vessels can be caught in a collection vessel. An adequate collection can usually be accomplished without milking the cord and is complete in approximately two minutes, before placental separation has occurred. Care should be taken to avoid contamination by maternal blood, urine, or other fluids in the delivery field. Umbilical cord blood can also be obtained by any other method known in the art.

A donor for the purposes of the present invention may include maternal donors who are donors for the purpose of informed consent for the donation, and are mothers with custodial rights of the actual newborn donors, with the actual donors of umbilical cord blood being the newborn babies. Maternal donors are individuals who are in good general health and between the ages of about 16 and about 50. Certain information may be collected from the maternal donor before or after cord blood donation in order to determine donor suitability and lack of transfusion transmitted infectious diseases, genetic diseases, and cancers of the hematopoietic system. For example, the maternal donor may be given a medical questionnaire to fill out. In one embodiment of the present invention, a maternal donor will undergo a medical examination before donation.

Collection of umbilical cord blood should be made under sterile conditions. Immediately upon collection, the cord blood should be mixed with an anticoagulant. Generally, from about 23 ml to about 35 ml of the anticoagulant is mixed with up to about 255 ml of cord blood (i.e., one cord blood unit). Suitable anticoagulants include any known in the art, such as, e.g., CPDA (citrate-phosphate-dextrose-adenosine), CPD (citrate-phosphate-dextrose), ACD (acid-citrate-dextrose), Alsever's solution (Alsever et al., *N.Y. St. J. Med.,* 41:126 (1941)), De Gowin's Solution (De Gowin et al., *J. Am. Med. Assoc.,* 114:850 (1940)), Edglugate-Mg (Smith et al., *J. Thorac. Cardiovasc. Surg.,* 38:573 (1959)), Rous-Turner Solution (Rous et al., *J. Exp. Med.,* 23:219 (1916)), other glucose mixtures, heparin, ethyl biscoumacetate, etc. Preferably, the anticoagulant is CPDA.

To aid cord blood processing and improve safety, processing bags for various blood components may be part of a sterile blood bag system. In one embodiment, a plasma storage solution may be incorporated into one of the processing bags. Additionally, both the collection bag and the processing bags may be equipped with ports and break connectors. The ports may be used for the addition or extraction of materials to or from the inside of the bag. A break connector may be used to temporarily close a tube or the entrance of a bag.

In addition to umbilical cord blood, placental or fetal blood can be used to produce the plasma-depleted blood compositions that are suitable for transplantation, e.g., to treat malignant diseases such as hematologic malignancies or benign diseases associated with the hematopoietic system. Placental or fetal blood can be obtained by any method known in the art. For example, fetal blood can be taken from the fetal circulation at the placental root with the use of a needle guided by ultrasound, placentocentesis, or fetoscopy. Placental blood can be obtained, e.g., by needle aspiration from the delivered placenta at the root and at distended veins.

In some embodiments, postnatal women are asked to donate cord blood and placental blood. Hospitals are contacted and asked to participate in a umbilical cord/placental blood collection project. Potential donors are women who are in labor and are about to deliver a baby either by natural delivery or Cesarean section. In U.S. Pat. No. 5,993,387, one method of obtaining umbilical cord blood and placental blood from postnatal women is described, e.g., by enrolling a family with a bank before a child is born and collecting a fee for the collection and storage of the cord stem cells to be collected after birth.

In one embodiment, after delivery, the cord blood and/or placenta is collected and examined. In some embodiments, examination ensures that the cord blood or placental blood is suitable for further processing. An examination may include examining the placenta to make sure it is intact and free from heavy meconium or purulent discharge. The umbilical cord may be examined to determine that it is intact with 2 arteries and 1 vein and devoid of true knots or other abnormalities. As described above, collection can be into a bag that preferably contains an anticoagulant such as a citrate-phosphate-dextrose-adenosine (CPDA) solution.

In preferred embodiments, after processing, the plasma-depleted UCB units contain a sufficient amount of stem cells for the successful transplantation of a child or an adult patient. Since true hematopoietic stem cells do not have convenient cell surface markers and can only be defined functionally, surrogates have to be used. For example, the total number of nucleated cells can often be predictive of the number of stem cells in a cord blood unit and has been shown to clinically correlate with engraftment and survival. In another example, the number of progenitor cells with cell surface markers such as CD34 or functional capabilities of forming various colony forming units are sometimes used, and are also correlated clinically with engraftment and survival.

After an anticoagulant has been added to and mixed with the cord blood, the resulting mixture can be stored at temperatures, e.g., between about 0° C. and about 42° C. or between about 15° C. and about 26° C., for up to about 48 hours.

Plasma Depletion Processing

The volume of the collected cord blood containing anticoagulant is reduced, e.g., by first centrifuging the mixture at temperatures between about 0° C. and about 42° C., preferably about between 15° C. and about 26° C. The centrifugation is done to remove a substantial volume of liquid, e.g., plasma, from the mixture. The centrifugation is preferably performed at about 1,000×g to about 2,500×g for between about 5 and about 20 minutes, with the centrifugal force and centrifugation time sufficient to cause sedimentation of most of the cells without causing cell damage. After centrifugation, a substantial volume of plasma is removed to reduce the volume of the cord blood mixture to produce a plasma-depleted cord blood unit that has not been depleted of red blood cells. In certain instances, at least about 10 ml of plasma is left in the plasma-depleted cord blood unit. The plasma-depleted unit is then transferred to a freezing container, e.g., a Cryocyte® bag, and cooled to between about 2° C. and about 8° C. for about 30 to about 60 minutes. In preferred embodiments, less than about 5% of the nucleated cells (e.g., less than about 5%, 4%, 3%, 2%, or 1%) are lost when the supernatant is removed, as evidenced by enumeration of cells in the supernatant plasma.

The acceptable volume is determined by the holding volume of the particular CryoCyte® bag used, the number of cells to be cryopreserved, and the concentration of the cryopreservant solution). If the volume of the plasma-depleted cord blood unit is too large as to cause the volume to exceed about 60 or about 75 ml, then a larger CryoCyte® bag can be used or the sample can be divided among two or more CryoCyte® bags.

Ex vivo Expansion of Stem Cells

Optionally, the hematopoietic stem cells present in the plasma-depleted cord blood unit can be multiplied using an in vitro culture technique either before or after cryopreservation, thereby expanding the number of stem cells available for therapy. Care should be taken to ensure that the ex vivo expansion of hematopoietic stem cells does not result in the production of differentiated progeny cells at the expense of multipotent stem cells that are therapeutically necessary for transplantation. Various protocols have been described for the growth of cord blood stem cells in culture (see, e.g., Smith et al., *Br. J. Haematol.*, 63:29-34 (1986); Dexter et al., *J. Cell. Physiol.*, 91:335 (1977); Witlock et al., *Proc. Natl. Acad. Sci. U.S.A.*, 79:3608-3612 (1982)). One skilled in the art will know of other procedures for expanding the population of stem cells in culture. Various factors can also be used for stimulating the proliferation of stem cells in vitro. As non-limiting examples, a variety of cytokines and growth factors such as interleukin-1 (IL-1), interleukin-3 (IL-3), interleukin-4 (IL-4), interleukin-6 (IL-6), granulocyte-macrophage (GM)-colony stimulating factor (CSF), alone or in combination, can be used to stimulate the ex vivo expansion of hematopoietic stem cells present in the plasma-depleted cord blood units of the present invention.

Cryopreservation and Storage

The freezing of cells is ordinarily destructive. On cooling, water within the cell freezes. Injury then occurs by osmotic effects on the cell membrane, cell dehydration, solute concentration, and ice crystal formation. As ice forms outside the cell, available water is removed from solution and withdrawn from the cell, causing osmotic dehydration and raised solute concentration that eventually destroys the cell. These injurious effects can be circumvented by: (a) use of a cryoprotectant; (b) control of the freezing rate; and/or (c) storage at a temperature sufficiently low to minimize cell death.

In preferred embodiments of the present invention, the plasma-depleted cord blood units are mixed with a cryoprotectant solution. Many cryoprotectants are known to those of skill in the art. Non-limiting examples of suitable cryoprotectants include, but are not limited to, dimethyl sulfoxide (DMSO), glycerol, ethylene glycol, propylene glycol, formamide, hydroxyethyl starch (HES), polyvinylpyrrolidine (PVP), albumin, choline chloride, amino acids, methanol, acetamide, glycerol monoacetate, inorganic salts, and low molecular weight polysaccharides such as dextran (e.g., Gentran® 40), sucrose, i-erythritol, D-ribitol, D-mannitol, D-sorbitol, i-inositol, or D-lactose. Preferably, the cryoprotectant solution comprises about a 10:1 ratio (volume/volume) of DMSO to Gentran® 40 such as, e.g., 50% DMSO to 5% Gentran® 40, which is added to provide a final concentration of from about 5% to about 10% DMSO and is pre-chilled to about 4° C. In certain instances, the cryoprotectant solution is mixed, loaded into a syringe, and the loaded syringe is cooled at between about 2° C. and about 8° C. for about 30 to about 60 minutes.

After cooling, the pre-chilled cryoprotectant solution is added to the plasma-depleted cord blood to form a cord blood mixture containing both anticoagulant and cryoprotectant. The cryoprotectant solution can be added to the plasma-depleted cord blood in the freezing container while the freezing container is in motion. For example, the freezing container can be placed on a rocking platform and maintained at a temperature between about 2° C. and about 8° C., e.g., by wrapping the freezing container in ice packs. In some embodiments, the cryoprotectant solution is added to the plasma-depleted cord blood in the freezing container using a programmable syringe pump. Syringe pumps are commercially available, from, e.g., J-KEM Scientific, Inc., New Era Pump Systems, Inc., and Kent Scientific. In a preferred embodiment, the cryoprotectant is added at a rate of about 0.75 ml per minute. As such, the rate of dilution is approximately a 1:100 dilution of the plasma-depleted cord blood unit per minute with the cryoprotectant solution. The acceptable rate of addition of the cryoprotectant to the plasma-depleted cord blood can be determined by the rate of dilution of the cryoprotectant solution, which is a factor of the rate of addition of the cryoprotectant, the volume of the plasma-depleted cord blood unit, and the concentration of the cryoprotectant solution.

The plasma-depleted cord blood mixture of the present invention containing both anticoagulant and cryoprotectant is typically stored in liquid nitrogen (e.g., in the liquid and/or vapor phase) at below about −135° C., preferably below about −150° C. The conditions for freezing the mixture are carefully controlled to enhance viability of cells after thawing. In some embodiments, the freezing container with the cryoprotectant-stem cell mixture is placed in an aluminum storage cassette that has been pre-cooled to between about 2° C. and about 8° C. The aluminum storage cassette, in some embodiments, is specially designed to have a window showing the bar code unit number of the stored cord blood unit and allows partial opening to allow for retrieval of attached segment samples of the unit without disturbing the bulk of the unit in the freezing bag. The aluminum storage cassette is then transferred to a controlled rate freezer, preferably within about 10 minutes of receiving the freezing container with the cord blood mixture containing anticoagulant and cryoprotectant. The mixture is then frozen at a controlled rate. The programmed rate of freezing is preferably about −1° C. per minute from about 4° C. to about −50° C. This freezing step can be preformed in the absence of a dip to compensate for the release of heat resulting from the phase transition (i.e., heat of fusion) of the composition from liquid to ice. After the initial freezing step, the processed cord blood units are further frozen at a rate of about −10° C. per minute from about −50° C. to about −90° C., with the temperature measured using a probe inside a dummy container in the same controlled rate freezer to mimic the conditions of the cord blood units being cryopreserved. Controlled rate freezers are commercially available from, e.g., FTS Systems and Thermo Forma.

The frozen cord blood mixture in the freezing container is then transferred to a liquid nitrogen tank for storage of the viable stem cells. The transfer is preferably in about 10 minutes or less, e.g., less than about 8 minutes, less than about 5 minutes, less than about 4 minutes, less than about 3 minutes, less than about 2 minutes, less than about 1 minute, less than about 45 seconds, less than about 30 seconds, less than about 20 seconds, or in about 10 seconds or less. Most preferably, the transfer takes about 1 minute or less.

Frozen cord blood units are preferably thawed quickly (e.g., in a water bath maintained at between about 37° C. and about 41° C.) and chilled immediately upon thawing. In certain instances, the freezing bag containing the frozen cord blood unit can be immersed in a warm water bath with optional gentle rotation to ensure mixing of the unit as it thaws and increase heat transfer from the warm water to the internal ice mass. In certain other instances, it may be desirable to treat the cord blood unit in order to prevent cellular clumping upon thawing by the addition before and/or after freezing of DNase, low molecular weight dextran and citrate, or hydroxyethyl starch (HES). As soon as the unit is in a slightly "slushy," state, the freezing bag can be placed in ice in preparation for administration. Exemplary protocols for thawing the plasma-depleted cord blood units of the present invention are provided in Examples 7 and 8 below.

In a preferred embodiment of the present invention, the thawed cord blood unit can be directly infused into a patient without a washing step. Thus, it is envisioned that plasma-depleted cord blood, cryopreserved and thawed but not washed, can be administered by direct infusion for therapeutic purposes. However, in instances where the cryoprotectant in a concentration effective for cryopreservation would be considerably toxic to a patient, it can be removed or diluted prior to administration. One technique for diluting the toxic concentration of cryoprotectant is by dilution and/or reconstitution to an insignificant concentration that is less toxic to cells. Preferably, this is accomplished by simply adding dilution/reconstitution solution, without including a washing step. In this case, the absolute amount of cryoprotectant, red blood cells, white blood cells, free hemoglobin, and lysed red cell ghosts infused into a recipient is similar to that for direct infusion. In certain other instances, diluting the toxic concentration of cryoprotectant is accomplished by adding a wash solution followed by one or more cycles of centrifugation to pellet cells, removal of the supernatant, and resuspension of the cells. After thawing and the optional removal of the cryoprotectant, cell count (e.g., by use of a hemocytometer) and cell viability testing (e.g., by trypan blue exclusion; see, below) can be performed to confirm cell survival.

Other procedures which can be used to further process the thawed cord blood units of the present invention include, but are not limited to, enrichment of stem cells and ex vivo expansion of stem cells. However, these steps can be omitted in order to minimize cell loss.

Determining Cell Viability

Cell viability can be determined at any point throughout the above-described process. In addition to stem cell viability, the number of cells can also be characterized, e.g., for nucleated and/or unnucleated cells. Those of skill in the art will recognize that many methods are available to determine cell viability. In some embodiments, cell viability is determined using dye exclusion assays, e.g., trypan blue dye exclusion. In some embodiments, samples of frozen cord blood are thawed and assayed for viability using dye exclusion assays. Using the methods herein, at least about 80%, or preferably about 85%, of nucleated cells are viable after thawing, or more preferably at least about 90%, 91%, 92%, 93%, 94%, 95%, 96%, 97%, 98%, 98%, or 99% of nucleated cells are viable after thawing.

Therapeutic Uses

The plasma-depleted, non-red blood cell (RBC)-depleted umbilical cord blood (UCB) compositions of the present invention are therapeutically valuable for a large number of diseases and disorders such as, e.g., those diseases and disorders associated with the hematopoietic system. The UCB compositions described herein are also valuable in the area of regenerative medicine, e.g., using stem cells to trigger the healing process or the regrowth of missing or damaged tissue in patients.

Non-limiting classes of diseases and disorders that can be treated by administering the UCB compositions of the present invention include malignant diseases such as hematologic malignancies and benign diseases associated with the hematopoietic system. Hematologic malignancies are a group of neoplasms that arise through malignant transformation of bone marrow derived cells.

Examples of hematologic malignancies and other types of malignant diseases include, but are not limited to, leukemias and lymphomas (e.g., acute lymphoblastic leukemia, acute myelogeneous leukemia, chronic myelogenous leukemia, juvenile chronic myelogenous leukemia, non-Hodgkin's lymphoma, juvenile myelomonocytic leukemia, biphenotypic leukemia, Burkitt's lymphoma, Hodgkin's lymphoma, multiple myeloma, chronic lymphocytic leukemia, acute undifferentiated leukemia, acute malignant myelosclerosis, polycythemia vera, agnogenic myelometaplasia, Waldenstrom's macroglobulinemia, acute bilineage leukemia, acute mast cell leukemia, chronic myelomonocytic leukemia, hairy cell leukemia, plasma cell leukemia, prolymphocytic leukemia, etc.), myelodysplastic disorders (e.g., refractory anemia with or without ringed sideroblasts, refractory anemia with excess blasts, refractory cytopenia, 5q syndrome, etc.), lymphoproliferative disorders, myelofibrosis, malignant tumors (e.g., breast cancer, neuroblastoma, malignant melanoma, carcinoma of the stomach, ovarian carcinoma, breast small cell lung carcinoma, retinoblastoma, testicular carcinoma, glioblastoma, rhabdomyosarcoma, tumors of the central nervous system, Ewing's sarcoma, etc.), and histiocytosis (e.g., Langerhans cell histiocytosis, familial erythrophagocytic lymphohistiocytosis, hemophagocytic lymphohistiocytosis, X-linked lymphoproliferative disease, etc.).

Examples of benign diseases associated with the hematopoietic system include, but are not limited to, hemoglobinopathies (e.g., thalassemia, sickle cell anemia, etc.), bone marrow failure syndromes (e.g., thrombocytopenia, amegakaryocytic thrombocytopenia, Blackfan-Diamond syndrome, dyskeratosis congenita, Fanconi anemia, osteopetrosis, reticular dysgenesis, sideroblastic anemia, Schwachman-Diamond syndrome, severe aplastic anemia, pancytopenia, agranulocytosis, red cell aplasia, idiopathic aplastic anemia, acquired idiopathic sideroblastic anemia, etc.), immune deficiencies (e.g., DiGeorge syndrome, lymphocyte adhesion disease, Nezelof's syndrome, Omenn syndrome, severe combined immune deficiency, Wiskott-Aldrich syndrome, X-linked hyper-IgM syndrome, alpha 1-antitrypsin deficiency, etc.), metablolic/storage diseases (e.g., aspartylglucosaminuria, adrenoleukodystrophy, alphamannosidosis, fucosidosis, Gaucher's disease, gangliosidosis, Hurler syndrome, Hurler-Scheie syndrome, Scheie syndrome, I-Cell disease, infantile ceroid lipofucoscinosis, Krabbe disease, Lesch-Nyhan syndrome, metachromatic leukodystrophy, Maroteaux-Lamy syndrome, sialidosis, Tay Sach disease, Wolman disease, mucopolysaccharidosis, mucolipidosis, etc.), disorders of neutrophils (e.g., chronic granulomatous disease, Chediak-Higashi syndrome, congenital neutropenia, Kostmann's syndrome, etc.), platelet diseases (e.g., Glanzmann's thrombobasthenia, etc.), porphyria (e.g., congenital erythropoietic porphyria, etc.), viral infections (e.g., HIV infection), and autoimmune disorders (e.g., systemic lupus erythematosus, rheumatoid arthritis, Sjogren's syndrome, type I diabetes, multiple sclerosis, chronic hepatitis, inflammatory osteopathies, etc.).

The plasma-depleted cord blood compositions of the present invention can also be of great value in the treatment of various genetic diseases and disorders affecting cells of the hematopoietic lineage. Examples of such diseases include, without limitation, thalassemia (e.g., alpha, beta, gamma), familial aplastic anemia, Fanconi's syndrome, Bloom's syndrome, pure red cell aplasia, familial erythrophagocytic lymphohistiocytosis, dyskeratosis congenital, Blackfan-Diamond syndrome, congenital dyserythropoietic syndromes I-IV, Chwachmann-Diamond syndrome, dihydrofolate reductase deficiency, formamino transferase deficiency, aspartyl glucosaminidase deficiency, beta-glucuronidase deficiency, hypoxanthine-guanine phosphoribosyltransferase deficiency, Lesch-Nyhan syndrome, congenital spherocytosis, congenital elliptocytosis, congenital stomatocytosis, congenital Rh null disease, paroxysmal nocturnal hemoglobinuria, glucose-6-phosphate dehydrogenase deficiency, pyruvate kinase deficiency, congenital erythropoietin sensitivity, sickle cell disease and trait, met-hemoglobinemia, severe combined immunodeficiency disease, severe combined immunodeficiency disease with absence of T and B cells, severe combined immunodeficiency disease with absence of T cells, severe combined immunodeficiency disease adenosine deaminase deficiency, bare lymphocyte syndrome, combined immunodeficiency, ionophore-responsive combined immunodeficiency, combined immunodeficiency with a capping abnormality, common variable immunodeficiency, nucleoside phosphorylase deficiency, granulocyte actin deficiency, neutrophil actin deficiency, infantile agranulocytosis, Gaucher's disease, adenosine deaminase deficiency, Kostmann's syndrome, reticular dysgenesis, and congenital leukocyte dysfunction syndromes.

As used herein, the term "thalassemia" refers to a group of genetic blood disorders. Individuals with thalassemia are not able to make enough normal hemoglobin due to unbalanced synthesis of the alpha or beta hemoglobin, which causes severe anemia. Hemoglobin is found in red blood cells and carries oxygen to all parts of the body. It consists of two different proteins, an alpha and a beta chain. If the body doesn't produce enough or has an imbalance of either of these two proteins, the red blood cells do not form properly and cannot carry sufficient oxygen. The result is anemia that begins in early childhood and lasts throughout life, requiring life-long frequent blood transfusions and iron chelation therapy to get rid of the iron overload from the frequent transfusions. Despite iron chelation therapy, organs eventually become overloaded with excess iron and are unable to function properly.

Individuals whose red blood cells do not produce enough alpha protein compared with the beta protein have alpha thalassemia. There are several types of alpha thalassemia that range from mild to severe in their effect on the body. The silent carrier state generally causes no health problems because the lack of alpha protein is so small that the hemoglobin functions normally. The hemoglobin constant spring condition is an unusual form of the silent carrier state that is caused by a mutation of the alpha globin gene. As in silent carrier state, an individual with this condition usually experiences no related health problems. The alpha thalassemia trait or mild alpha thalassemia condition is characterized by the somewhat greater lack of alpha protein. Patients with this condition have smaller red blood cells and a mild anemia, although many patients do not experience symptoms. Hemoglobin H disease is characterized by a lack of alpha protein that is great enough to cause severe anemia and serious health problems such as an enlarged spleen, bone deformities, and fatigue. Hemoglobin H-constant spring disease is a condition that is more severe than hemoglobin H disease. Individuals with this condition tend to have a more severe anemia and suffer more frequently from enlargement of the spleen and viral infections. Homozygous constant spring disease is a variation of hemoglobin H-constant spring that occurs when two constant spring carriers pass their genes on to their child. This condition is generally less severe than hemoglobin H constant spring and more similar to hemoglobin H disease. Hydrops fetalis or alpha thalassemia major is characterized by the absence of alpha genes, which causes the gamma globins produced by the fetus to form an abnormal hemoglobin called hemoglobin Barts. Most individuals with this condition die before or shortly after birth. In some extremely rare cases where the condition is discovered before birth, in utero blood transfusions have allowed the birth of children with hydrops fetalis who then require lifelong blood transfusions and medical care. In utero hematopoietic stem cell transplantation, including cord blood transplantation, can also be performed to cure this condition.

Individuals whose red blood cells do not produce enough beta protein have beta thalassemia. There are several types of beta thalassemia that range from mild to severe in their effect on the body. Thalassemia minor or thalassemia trait is characterized by a lack of beta protein that is not great enough to cause problems in the normal functioning of hemoglobin. An individual with this condition simply carries the genetic trait for thalassemia and will usually experience no health problems other than a possible mild anemia. Thalassemia intermedia is a condition where the lack of beta protein in the hemoglobin is great enough to cause a moderately severe anemia and significant health problems, including bone deformities and enlargement of the spleen. Thalassemia major or Cooley's anemia is the most severe form of beta thalassemia, in which the complete lack of beta protein in the hemoglobin causes a life-threatening anemia that requires regular blood transfusions and extensive ongoing medical care. These extensive, lifelong blood transfusions lead to iron-overload which must be treated with chelation therapy to prevent early death from organ failure.

In addition to the different types of alpha and beta thalassemias described above, there are other related disorders such as E beta thalassemia and sickle beta thalassemia. Such conditions are also suitable for treatment by administering the plasma-depleted cord blood compositions of the present invention.

In certain instances, the plasma depleted cord blood compositions of the present invention contain hematopoietic stem cells that do not carry the genetic defect found in the patient or do not carry the genetic defect in a homozygote state or in a double heterozygote state and thus are capable of giving rise to a normally functioning hematopoietic system. In certain other instances, the hematopoietic stem cells in the cord blood compositions of the present invention have stably incorporated a heterologous gene capable of expression by their progeny cells and such recombinant stem cells can be used in the treatment of genetic disorders of the hematopoietic system. For example, patients who have hematopoietic cells which lack a gene or have a mutant gene can be infused with hematopoietic stem cells that have incorporated a functional counterpart of the deficient gene. Such genes which can be subject to gene therapy include, but are not limited to, hemoglobin or enzymes which mediate its synthetic pathway, e.g., for treatment of anemias such as beta-thalassemia, sickle-cell disease, etc.

Numerous techniques are known in the art for the introduction of foreign genes into cells and may be used to construct the recombinant hemapoietic stem cells for purposes of gene therapy. The technique used should provide for the stable transfer of the heterologous gene sequence to the stem cell, so that the heterologous gene sequence is heritable and expressible by stem cell progeny, and so that the necessary developmental and physiological functions of the recipient cells are not disrupted. Techniques which may be used include, but are not limited to, cell fusion, chromosome-mediated gene transfer, micro cell-mediated gene transfer, transfection, transformation, transduction, electroporation, infection (e.g., recombinant DNA viruses, recombinant RNA viruses), spheroplast fusion, microinjection, DEAE dextran, calcium phosphate precipitation, liposomes, lysosome fusion, synthetic cationic lipids, use of a gene gun or a DNA vector transporter, etc. For various techniques for transformation or transfection of mammalian cells, see, e.g., Keown et al., *Methods Enzymol* 185:527-37 (1990); Sambrook et al., Molecular Cloning, A Laboratory Manual, Third Edition, Cold Spring Harbor Laboratory Press, N.Y. (2001).

Other diseases and disorders that can be treated with the plasma-depleted cord blood compositions of the present invention include, without limitation, myelosclerosis, acquired hemolytic anemias, acquired immunodeficiencies, infectious disorders causing primary or secondary immunodeficiencies, bacterial infections (e.g., Brucellosis, Listerosis, tuberculosis, leprosy), parasitic infections (e.g., malaria, Leishmaniasis), fungal infections, disorders involving disproportions in lymphoid cell sets and impaired immune functions due to aging, phagocyte disorders (e.g., neutrophil actin deficiency, neutrophil membrane GP-180 deficiency), inherited erythrocyte abnormalities, inherited immune system disorders, inherited lymph and heme line disorders, inherited metabolic disorders, inherited platelet disorders, plasma cell disorders, other malignancies, other non-malignant diseases, congenital thrombosis, ataxia-telangiectasia, cartilage-hair hypoplasia, glucose storage disease, HIV infection, hemophagocytosis, Hunter syndrome, immune deficiency and neutropenia, leukocyte adhesion deficiency, lysosomal storage disease, myelofibrosis with myeloid metaplasia, Morquio syndrome, Niemann-Pick disease, neuronal ceroid lipofuscinosis, and Sanfilippo syndrome types A, B, C, and D.

The plasma-depleted cord blood compositions described herein are also valuable in the area of regenerative medicine, e.g., using stem cells to trigger the healing process or the regrowth of missing or damaged tissue in patients. For example, one or more plasma-depleted cord blood units can be administered to a patient for regenerative therapies to heal broken bones or to treat bad burns, blindness, deafness, heart damage (e.g., due to heart attack, etc.), nerve damage (e.g., spinal cord injury), stroke, Parkinson's disease, Alzheimer's disease, diabetes (type I or II), and other conditions.

The plasma-depleted cord blood compositions of the present invention maximize the total nucleated cell dosage through the processing, cryopreservation, selection, and/or thawing procedures described herein to provide the maximal amount of hematopoietic stem cells in a given cord blood unit. As a result, patients having any of the above-described diseases or disorders experience a clinical outcome that is superior to those achieved with whole blood or RBC-depleted cord blood units. In particular, patients display significant improvement in parameters such as the cumulative incidence and speed to neutrophil and platelet engraftment, extent of disease-free survival, relapse rate, transplant-related mortality, and overall survival.

IV. Examples

The present invention will be described in greater detail by way of the following examples. The following examples are offered for illustrative purposes, and are not intended to limit the present invention in any manner. Those of skill in the art will readily recognize a variety of noncritical parameters which can be changed or modified to yield essentially the same results.

Example 1

Exemplary Plasma-Depleted Umbilical Cord Blood Unit

This example provides an exemplary umbilical cord blood (UCB) composition that has been substantially depleted of plasma but not depleted of red blood cells.

Standard cryoprotectant volume: about 15 ml of cryoprotectant for about 60 ml of plasma-depleted unit.

If CV=collected cord blood volume, AV=anticoagulant volume (e.g., between about 23 to about 35 ml), PV=plasma-depleted cord blood volume, PAV=post-processing anticoagulant volume; and APV=anticoagulated plasma-depleted cord blood volume, then an exemplary UCB composition of the present invention would comprise:

PV=60 ml×(CV/(CV+AV));

PAV=60 ml×(AV/(CV+AV));

PV+PAV=APV=60 ml; and

Pre-freeze volume=APV+cryoprotectant volume=60 ml+15 ml=75 ml.

Example 2

Plasma Depletion of Umbilical Cord Blood Units Increases Hematocrit and Red Blood Cell Concentration This example illustrates that processing collected umbilical cord blood (UCB) according to the methods of the present invention increases the hematocrit (i.e., percentage of red blood cells in the final volume) and red blood cell (RBC) concentration of the UCB units.

UCB collected from 488 newborns were assayed to determine the hematocrit ("PRE-HCT %") and RBC concentration ("PRE-RBC ($10^6/\mu l$)") of the samples prior to the plasma depletion processing described herein. After processing, the hematocrit ("POST-HCT %"), RBC concentration ("POST-RBC ($10^6/\mu l$)"), and white blood cell concentration ("POST-WBC ($10^3/\mu l$)") were determined. As shown in Table 3, processing UCB units by plasma depletion according to the methods of the present invention provides a substantial increase in the hematocrit and RBC concentration.

TABLE 3

Pre- and Post-Processing Numbers for 488 Umbilical Cord Blood Units.

| | PRE-HCT % | PRE-RBC ($10^6/\mu l$) | POST-HCT % | POST-RBC ($10^6/\mu l$) | POST-WBC ($10^3/\mu l$) |
|---|---|---|---|---|---|
| Average | 39.7 | 3.5 | 65.1 | 5.7 | 22.3 |
| Median | 39.8 | 3.4 | 66.5 | 5.9 | 17.7 |

Without being bound to any particular theory, the higher hematocrit and/or higher RBC concentration of the post-processed UCB units advantageously provide better cryopreservation properties and/or improved clinical outcome.

Example 3

Comparison of Plasma-Depleted, Red Blood Cell-Depleted, and Whole Blood Umbilical Cord Blood Units This example illustrates a comparison of the plasma-depleted cord blood compositions of the present invention with whole blood and HES red blood cell-depleted units.
Hematocrit:
Plasma-depleted (PD) umbilical cord blood (UCB) units have on average about 1.8 times the hematocrit of whole blood units or red blood cell-depleted (RD) units. The hematocrit corresponds to the percentage of red blood cells (RBC) by volume for a given unit. Without being bound to any particular theory, the higher hematocrit of the PD UCB units of the present invention advantageously provide better cryopreservation properties and/or improved clinical outcome.

| Hematocrit | | |
|---|---|---|
| Whole Blood | PD Blood | RD Blood |
| ≦40% | ≧50% | ≦50% |

Red Blood Cell Concentration:
PD units have on average about 1.8 times the RBC concentration of whole blood and RD units. Without being bound to any particular theory, the higher RBC concentration of the PD UCB units of the present invention advantageously provide better cryopreservation properties and/or improved clinical outcome.

| RBC Concentration | | |
|---|---|---|
| Whole Blood | PD Blood | RD Blood |
| <$3.2 \times 10^6/\mu l$ | ≧$3.2 \times 10^6/\mu l$ | <$3.2 \times 10^6/\mu l$ |

Plasma Volume:
PD and RD UCB units have a lower percentage of plasma by volume than whole blood units.

| Plasma Volume | | |
|---|---|---|
| Whole Blood | PD Blood | RD Blood |
| 50-60% | 0-30% | 0-30% |

White Blood Cell Number:
PD UCB units have similar white blood cell (WBC) numbers as whole blood and RD units.

| WBC Number | | |
|---|---|---|
| Whole Blood | PD Blood | RD Blood |
| ≧$90 \times 10^7$ | ≧$90 \times 10^7$ | ≧$90 \times 10^7$ |

White Blood Cell Concentration:
PD units have a WBC concentration between whole blood and RD units, with about 1.8 times the WBC concentration of whole blood, while RD units have about 3 times WBC concentration of whole blood.

| WBC Concentration | | |
|---|---|---|
| Whole Blood | PD Blood | RD Blood |
| $8 \times 10^3/\mu l$ | $15 \times 10^3/\mu l$ | $24 \times 10^3/\mu l$ |

Red Blood Cell Number:
PD and whole blood units have similar numbers of RBC, which is about 5 times greater than RD units.

| RBC Number | | |
| --- | --- | --- |
| Whole Blood | PD Blood | RD Blood |
| 1 to 2.5 × $10^9$ | 1 to 2.5 × $10^9$ | 0.2 to 0.5 × $10^9$ |

CD34+ Cell Number:
PD units have similar CD34+ cell numbers as whole blood and RD units.

| CD34+ Cell Number | | |
| --- | --- | --- |
| Whole Blood | PD Blood | RD Blood |
| 1 × $10^6$ to 5 × $10^7$ | 1 × $10^6$ to 5 × $10^7$ | 1 × $10^6$ to 5 × $10^7$ |

% CD34+ Cells in WBC Fraction:
PD units have a percentage of CD34+ cells in the WBC fraction that is between whole blood and RD units.

| % of CD34+ Cells in WBC Fraction | | |
| --- | --- | --- |
| Whole Blood | PD Blood | RD Blood |
| 0.08%-1.0% | 0.15%-1.8% | 0.24%-3.0 |

Number of Nucleated Cells:
PD units have total nucleated cell (TNC) numbers that are similar to whole blood and RD units.

| Number of Nucleated Cells | | |
| --- | --- | --- |
| Whole Blood | PD Blood | RD Blood |
| 90-300 × $10^7$ | 90-300 × $10^7$ | 90-300 × $10^7$ |

% Nucleated Cells in Cellular Fraction:
PD units have a percentage of nucleated cells in the cellular fraction that is between whole blood and RD units.

| % of Nucleated Cells in Cellular Fraction | | |
| --- | --- | --- |
| Whole Blood | PD Blood | RD Blood |
| 0.3% | 0.54% | 1% |

Example 4

Hematopoietic Stem Cell Transplantation (HSCT) Using Umbilical Cord Blood (UCB) Units Depleted of Plasma But Not of Red Blood Cells This example illustrates that umbilical cord blood (UCB) units that have been substantially depleted of plasma, but not depleted of red blood cells are a safe and effective source of hematopoetic stem cells with a clinical outcome that is, in most instances, superior to historical controls, and that not washing plasma-depleted (PD) UCB units after thawing improves the incidence to platelet engraftment and the time to engraftment for neutrophils and platelets.

UCB is an attractive source for hematopoetic stem cell transplantation (HSCT) because of the less stringent HLA matching requirements and lower graft-versus-host disease incidence and severity. However, unlike bone marrow or peripheral blood sources, the limiting cell dose associated with UCB units have hampered its widespread use in adults. The red cell depletion techniques that are widely used in the field are the hydroxyethyl starch (HES) and the Ficoll methods, both of which incur significant nucleated cell loss after processing that further exacerbates the cell dosage limitation. Of the many strategies to increase the cell dosage of UCB units including double unit transplants, combined UCB/haploidentical transplants, and ex vivo expansion, the approach described in this example advantageously increases the recovery of nucleated cells during processing and thawing by depleting plasma, but not red blood cells. As a result, entrapment of nucleated cells and progenitor and stem cells is avoided, with some degree of volume reduction associated with the removal of plasma. Usage of this method results in loss of less than 0.1% nucleated cells in the discarded plasma fraction after processing (n=27).

The approach described in this example also increases the recovery of nucleated cells by removing the washing step after thawing of frozen UCB. Washing after thawing of frozen cord blood units is widely practiced for the purpose of removal of the cryoprotectant DMSO and free hemoglobin from lysed red cells (Kurtzberg et al., *NEJM*, 335:157-166 (1996)). For example, better post-thaw viability with washing has been reported (Rubinstein et al., *PNAS*, 92:10119-10122 (1995)). In addition, removal of cryoprotectant before infusion has been reported to facilitate faster engraftment (Kurtzberg et al., supra). Recently, however, several reports call into question the role of post-thaw washing of cord blood units prior to infusion into patients (Nagamura-Inoue et al., *Transfusion*, 43:1285-1294 (2003); Hahn et al., *Bone Marrow Transplantation*, 32:145-150 (2003); Antoneanas et al., *Bone Marrow Transplantation*, 34:739 (2004); Creer et al., Proceedings of the $3^{rd}$ Annual International Cord Blood Transplantation Symposium). In these studies, similar clinical outcome and post-thaw viability are seen with the standard red cell depleted cord blood units whether or not washing was employed after thawing. No such data exists on the utility of post-thaw washing for cord blood units that were depleted of plasma, but not depleted of red blood cells.

A large and racially diverse PD UCB inventory was established, with over 162 UCB HSCTs performed using such products all over the world as of April 2005. The design of the study is shown below:

Study Design

1. Inclusion criteria—all transplants between November 2001 and April 2005: n=162.
2. # transplant data not yet available: n=44.
3. Data supplied and audited by NMDP and transplant centers.
4. "All Patients"—engraftment or survival data available for 118 of 162 transplanted −73%.
5. 44 out of 162 data not yet available −27%.
6. Data available for 58 out of 64 NMDP transplants −91%.
7. Data available for 89 out of 117 U.S. transplants −76%.
8. Data available for 29 out of 45 Taiwan transplants −64%.

9. "Relapse/re-transplant" transplants (prior transplant and/or transplanted during relapse)=20.
10. "Remission/1st transplant" patients=98 (remission patients without prior transplants).
11. Single UCB transplants=99; double UCB transplants=19; non-myeloablative=7; UCB/haploidentical PSCT=1.

As indicated in the study design, engraftment and/or survival data were available for 118 patients, representing a 73% overall data collection rate. The characteristics of these 118 patients is shown below:

Patient Characteristics

1. Sex: M=72 (61%); F=56 (39%).
2. Age: Average=14; Median=8; Range=0.3-55.
   31 transplants in patients over age 16 (26%).
3. Weight: Average=35 kg; Median=26 kg; Range=4.5-103 kg.
   36 transplants in patients over 50 kg (31%).

Benign indications accounted for 29 cases (25%), with 14 hemoglobinaphthies, 6 aplastic anemias, 5 Wiscott-Aldrich Syndrome (WAS), 2 severe combined immunodeficiency syndrome (SCID), and 2 others. There were 89 transplants for malignant indications (75%), with 37 acute lymphoblastic leukemia (ALL), 22 acute myelogenous leukemia (AML), 9 chronic myelogenous leukemia (CML), and 21 others. There were 20 transplants (22% of malignant) where patients were at 1CR/1CP, 20 transplants (22% of malignant) where patients were relapse/re-transplant patients, 7 transplants where patients had prior transplants, and 16 transplants where patients were transplanted during relapse, induction failure, resistant tumor, or blast crisis.

The PD UCB units of all 118 patients were characterized by a median pre-freeze total nucleated cell (TNC) dose of $5.6 \times 10^7$/kg with an average pre-freeze TNC dose of $7.6 \times 10^7$/kg. The median post-thaw TNC dose (n=68) was $5.2 \times 10^7$/kg (93% recovery) and the average post-thaw TNC dose was $7.9 \times 10^7$/kg (100% recovery). The median pre-freeze CD34 dose (n=117) was $1.8 \times 10^5$/kg with an average pre-freeze CD34 dose of $2.6 \times 10^5$/kg. The median number of HLA ABDR matches was 4.0, with class I at low to intermediate resolution and class II at high resolution. Median post-thaw viability per transplant center was 75%. 41 of the transplants (35%) were performed outside of the United States. 89 (75% with 58 NMDP and 31 non-NMDP) of the transplants used cord blood from StemCyte U.S. as the source; 29 (25%) of the transplants used cord blood from StemCyte Taiwan.

Clinical outcome on the 118 patients with available engraftment or survival outcome data who were transplanted with PD UCB units indicated that the unadjusted cumulative incidence of engraftment for ANC500, Plt20K, and Plt50K were 90±3% (FIG. 1A), 77±5% (FIG. 1B), and 75±5%, respectively. Since the cumulative incidence was unadjusted, all deaths prior to the expected time to engraftment were treated as graft failures. The median time to engraftment for ANC500 (n=87), Plt20K (n=72), and Plt50K (n=68) were 22.0 (range 7-64), 49.5 (range 13-95), and 58.5 days (range 21-132), respectively. As shown in Table 4, the cumulative incidence of engraftment and median time to engraftment for PD UCB transplant patients was substantially higher as compared to patients transplanted with RD UCB units from the New York Blood Center (NYBC) or the National Marrow Donor Program (NMDP).

TABLE 4

PD UCB units provide superior clinical outcome compared to RD UCB units.

|  | Cumulative incidence of ANC500 engraftment | Median time to ANC500 engraftment (Range) | Cumulative incidence of Plt20K engraftment | Median time to Plt20K engraftment (Range) | Cumulative incidence of Plt50K engraftment | Median time to Plt50K engraftment (Range) | One-year survival rate |
|---|---|---|---|---|---|---|---|
| PD UCB units (All patients) | 90 ± 3% (unadjusted) | 22 days (7-64) | 77 ± 5% (unadjusted) | 49.5 days (13-95) | 75 ± 5% (unadjusted) | 58.5 days (21-132) | 65 ± 5% |
| PD UCB units (Remission first patients) | 94 ± 3% (unadjusted) | 22 days | 81 ± 5% (unadjusted) | 49.5 days | 80 ± 5% (unadjusted) | 58 days | 73 ± 5% |
| NYBC RD UCB units | 72% (unadjusted) | 28 days (10-120) | 50 ± 7% (unadjusted) |  | 58% (adjusted)* | 90 days (16-250) | 40-45% |
| NMDP RD UCB units | 87 ± 4% (adjusted)* | 21 days (8-62) | 61 ± 7% (adjusted)* | 64 days (12-473) |  |  | 45 ± 8% |
| St. Louis RD UCB units |  |  |  |  |  |  | 54% |

*Adjustment excludes death prior to day 21, resulting in a higher apparent engraftment.

58/118 (49%) of the patient data was audited and supplied by NMDP and re-audited by transplant centers; the remainder was audited and supplied by transplant centers. The unadjusted cumulative incidence of engraftment for absolute neutrophil count of 500 (ANC500), platelet count of 20,000 (Plt20K), and platelet count of 50,000 (Plt50K) were calculated. All cumulative incidence rates were calculated without adjustment, that is, all deaths prior to engraftment were counted as graft failures. Kaplan Meier estimates were used to analyze survival and disease free survival.

With a median follow-up of 526 days (range 106-1,284 days) for the surviving patients, the Kaplan-Meier estimates of 1-year survival for all cases and disease-free survival (DFS) for malignant cases at 1 year were 65±5% (FIG. 1C) and 50±6% (FIG. 1D), respectively. Table 4 also shows that the one-year survival rate for PD UCB transplant patients was substantially higher as compared to patients transplanted with RD UCB units from the NYBC, NMDP, or St. Louis Cord Blood Bank. The incidence of grade III-IV acute graft-versus-host disease (GvHD) and chronic GvHD were 15% at 100 days and 13% at 1 year, respectively, which are lower than the values previously reported. The relapse rate for malignant cases and the transplant related mortality (TRM) rate for all cases were 25±6% at 1 year and 26±4% at 1 year, respectively. These results indicate that patients receiving the PD UCB units of the present invention achieve superior clinical outcome (e.g., improved cumulative incidence of ANC500, Plt20K, and Plt50K engraftment, faster median time to ANC500, Plt20K, and Plt50K engraftment, and increased one-year survival rate) relative to patients transplanted with RD or whole blood UCB units. In addition, the GvHD, 1-year survival rate, and disease-free survival rate of transplantation with PD UCB units are superior as compared to bone marrow and peripheral blood stem cell transplants.

Figure 2:
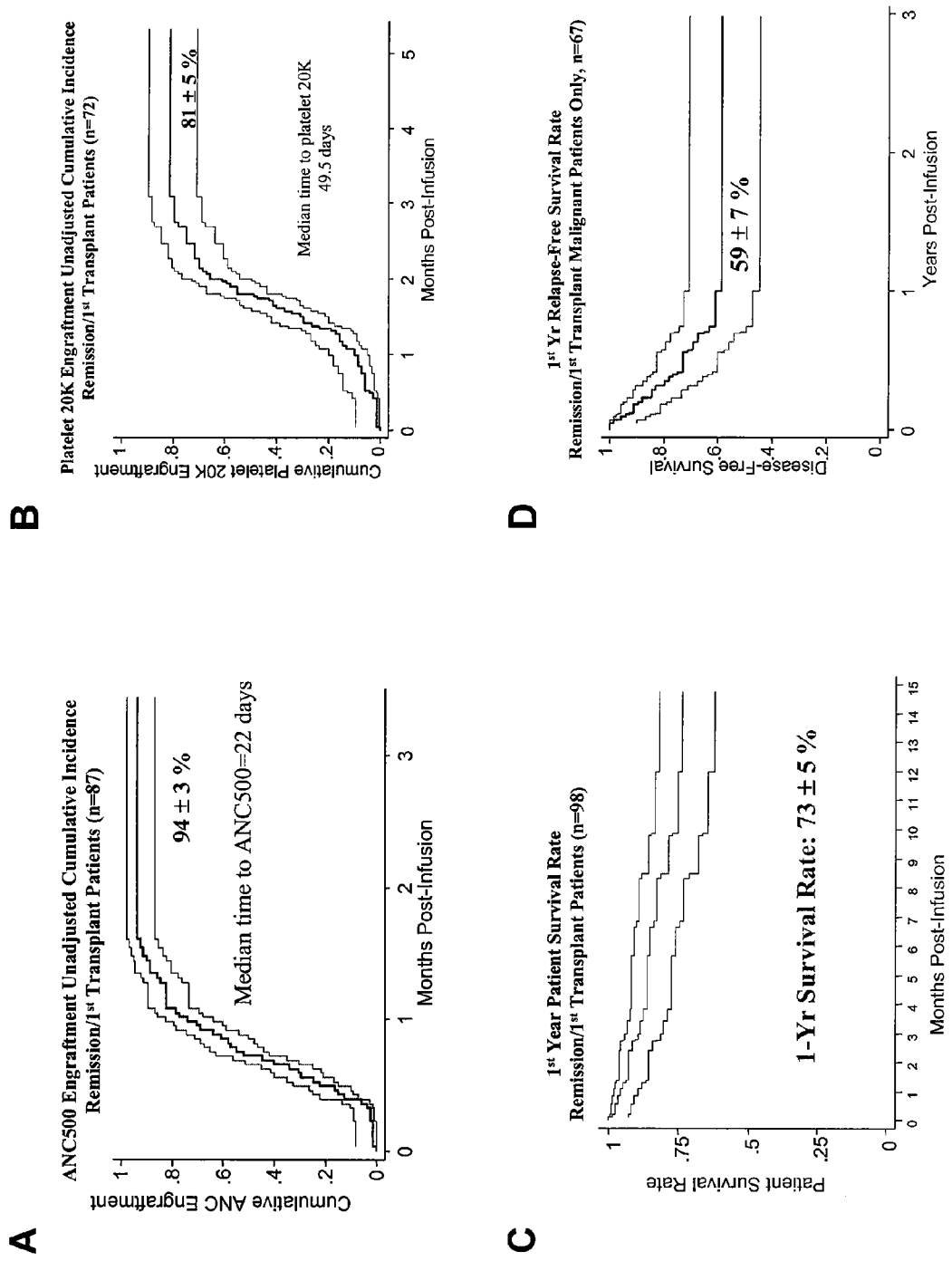
FIG. 2 shows the results for the remission $1^{st}$ transplant subset of patients.

When the remission first transplant patients (i.e., patients with no prior transplants and patients who were transplanted during remission; n=98) were analyzed separately, the unadjusted cumulative incidence of engraftment for ANC500, Plt20K, and Plt50K were 94±3% (FIG. 2A), 81±5% (FIG. 2B), and 80±5%, respectively. The median time to engraftment for ANC500, Plt20K, and Plt50K were 22.0, 49.5, and 58.0 days, respectively. The Kaplan-Meier estimates of 1-year survival for all cases and disease-free survival (DFS) for malignant cases at 1 year were 73±5% (FIG. 2C) and 59±7% (FIG. 2D), respectively. The relapse rate for malignant cases and the TRM rate for remission patients were 20±6% at 1 year and 20±4% at 1 year, respectively. Table 4 shows that the remission first PD UCB transplant patients have dramatically improved cumulative incidence of ANC500, Plt20K, and Plt50K engraftment, faster median time to ANC500, Plt20K, and Plt50K engraftment, and increased one-year survival rate relative to patients transplanted with RD UCB units. These results demonstrate that HSCT using PD UCB can be performed safely and effectively.

Figure 3:
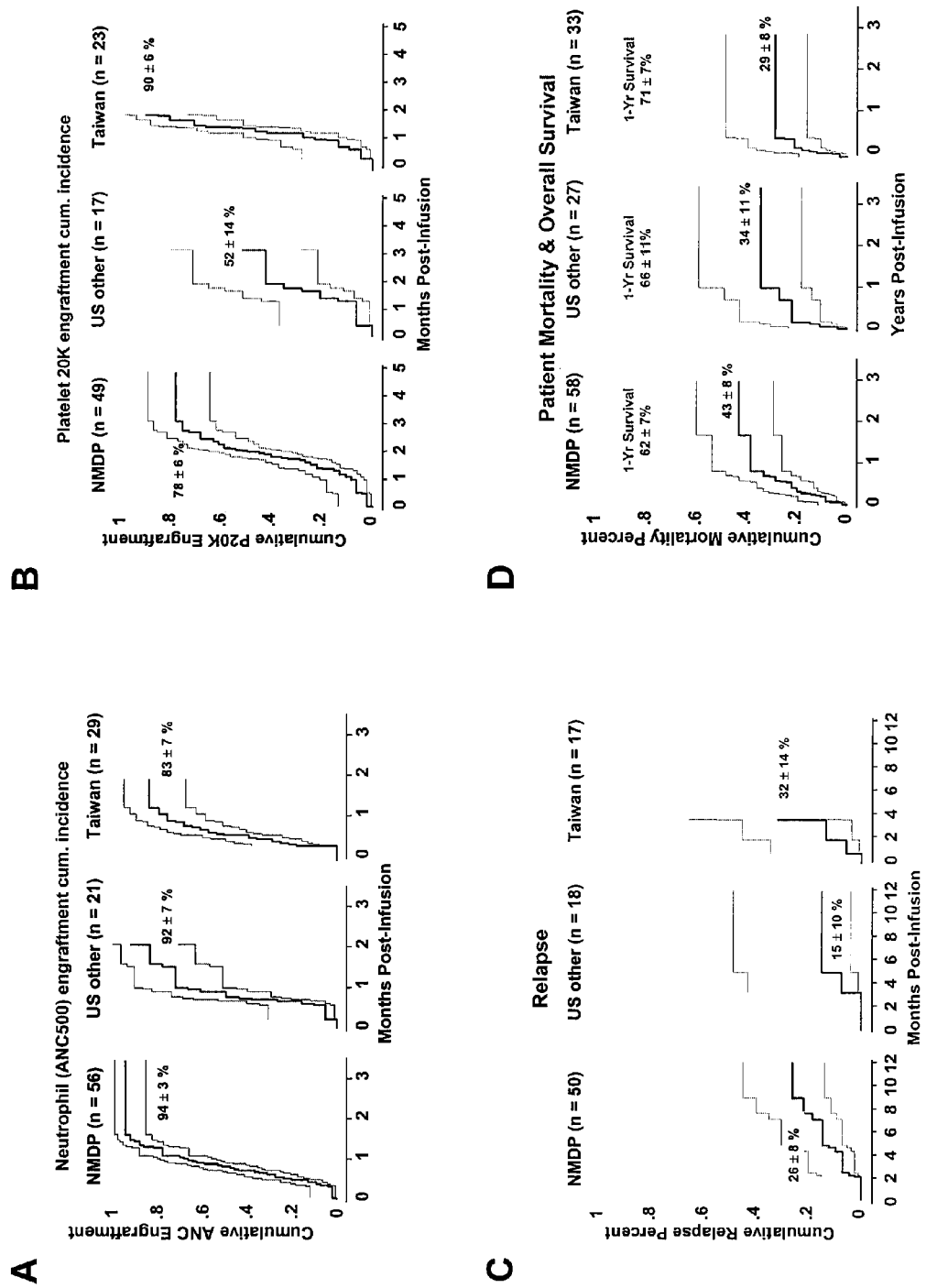
FIG. 3 shows a comparison between NMDP, non-NMDP U.S., and non-NMDP Taiwan patients.

A comparison between NMDP vs. Non-NMDP U.S. and Non-NMDP Taiwan patients was also performed. In particular, FIG. 3 shows a comparison of the cumulative incidence of ANC500 engraftment (FIG. 3A), the cumulative incidence of platelet 20K engraftment (FIG. 3B), the relapse rate (FIG. 3C), and the patient mortality and 1-year survival rates (FIG. 3D) for these three subsets of patients. Because the NMDP outcome data collection rate is over 91% of the patients, favorable reporting bias by transplant centers is essentially eliminated. By comparing non-NMDP subsets to NMDP results and finding essentially similar results, by extrapolation, significant favorable reporting bias is ruled out in those groups as well.

Figure 4:
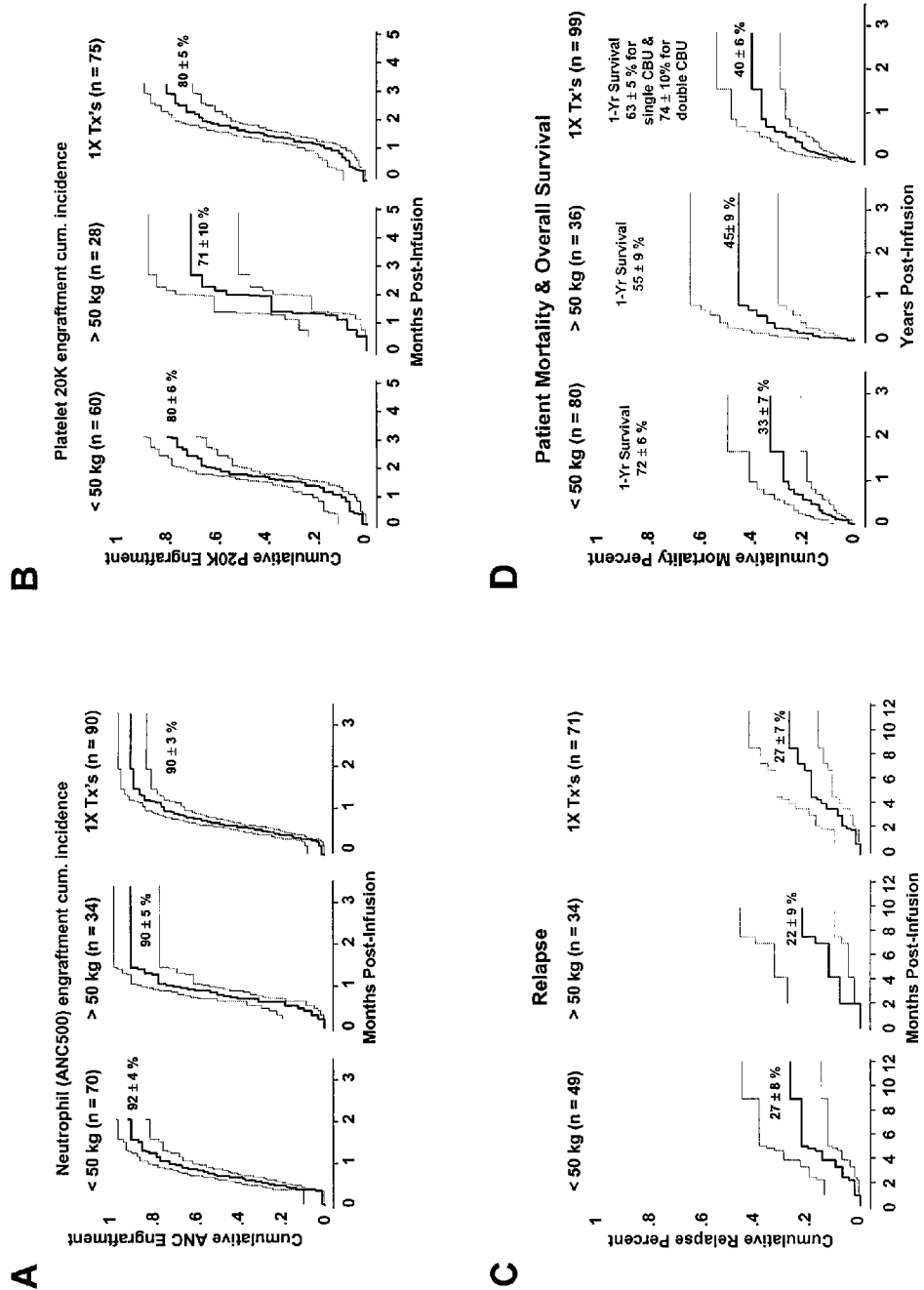
FIG. 4 shows a comparison between pediatric, adult, and single unit transplant patients.

A comparison between subsets of patients in the pediatric weight group (<50 kg), adult weight group ($\geq$50 kg), and single unit transplants was also performed. In particular, FIG. 4 shows a comparison of the cumulative incidence of ANC500 engraftment (FIG. 4A), the cumulative incidence of platelet 20K engraftment (FIG. 4B), the relapse rate (FIG. 4C), and the patient mortality and 1-year survival rates (FIG. 4D) for these three subsets of patients. This comparison shows that the adult weight patients achieved outstanding and superior results relative to, e.g., Laughlin et al., *NEJM* 351: 2265 (2004) and Rocha et al., *NEJM* 351:2276-85 (2004). The pediatric results are outstanding when compared to the age-stratified results from the NYBC. The single unit results show that contribution by a second unit from another center is not responsible for the outstanding clinical outcome.

Figure 5:
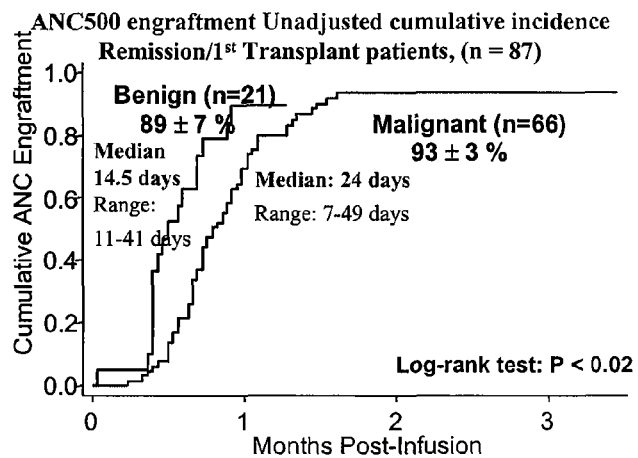
FIG. 5 shows a comparison between patients with benign or malignant diseases.
Figure 5:
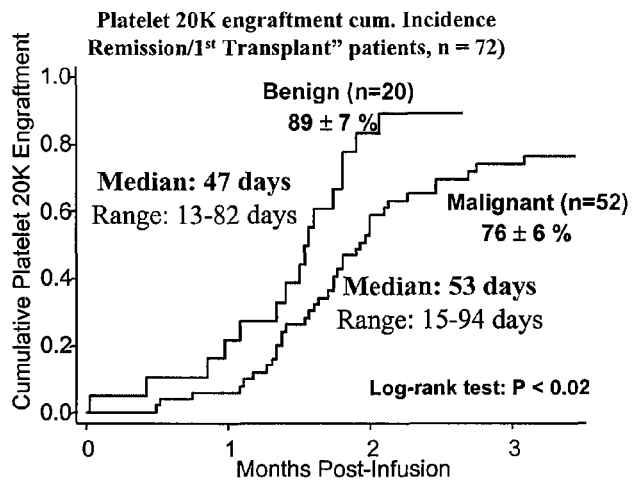
Figure 5:
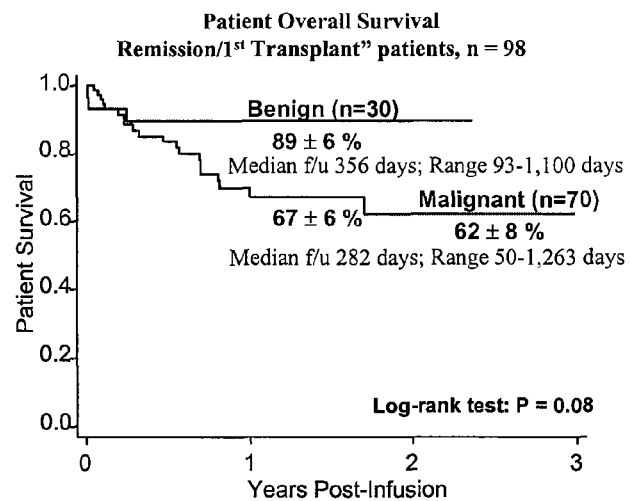

A comparison between patients with benign or malignant diseases in the remission subset was also performed. In particular, FIG. 5 shows a comparison of the cumulative incidence of ANC500 engraftment (FIG. 5A), the cumulative incidence of platelet 20K engraftment (FIG. 5B), and the 1-year survival rate (FIG. 5C) for these two subsets of patients.

With regard to hematopoetic stem cell transplantation for benign indications, the median pre-freeze TNC dose was $7.7 \times 10^7$/kg, the median post-thaw TNC dose was $7.7 \times 10^7$/kg, and the median pre-freeze CD34 dose was $3.1 \times 10^5$/kg. The median time to engraftment for ANC500 (n=21), Plt20K (n=20), and Plt50K (n=18) were 14.5 days (range 11-41), 47.0 days (range 13-82), and 56.5 days (range 21-96), respectively. The unadjusted cumulative incidence of engraftment for ANC500, Plt20K, and Plt50K were 89±7%, 89±7%, and 87±8% respectively. The incidence of reported grade II acute GvHD was 33%, and none of the patients had grade III-IV acute GvHD. 50% developed limited chronic GvHD (7/14), and so far only one patient was reported to have extensive chronic GvHD. With a median follow-up of 356 days (range 93-1,100 days), the Kaplan-Meier estimates of 1-year TRM, overall survival, and disease-free survival were 11±6%, 89±6%, and 89±6%, respectively.

With regard to hematopoetic stem cell transplantation for malignant indications, the median pre-freeze TNC dose was $6.4 \times 10^7$/kg, the median post-thaw TNC dose was $5.3 \times 10^7$/kg, and the median pre-freeze CD34 dose was $2.5 \times 10^5$/kg. The median time to engraftment for ANC500 (n=66), Plt20K (n=52), and Plt50K (n=50) were 24 days (range 7-49 days), 53 days (range 15-94 days), and 63 days (range 37-132 days), respectively. The unadjusted cumulative incidence of engraftment for ANC500, Plt20K, and Plt20K were 93±3%, 76±6%, and 75±6%, respectively. The incidence of reported grade II-IV and III-IV acute GvHD were 37% and 20%, respectively. 12% of patients developed limited chronic GvHD and 15% developed extensive chronic GvHD. With a median follow-up of 282 days (range 50-1,263 days), the Kaplan-Meier estimates of 1-year TRM, overall survival, and relapse-free survival were 20±6%, 67±6% and 59±7%, respectively.

No major adverse events were associated with infusion of PD UCB transplants whether the units were washed or not after thawing. Common side-effects reported included hemoglobinuria, hypertension, hives, nausea and vomiting, and dyspnea. Hemoglobinuria occurred more frequently in patients that received unwashed cord blood. One patient developed transient seizure and encephalopathy that appeared to be temporally related to the infusion of unwashed cord blood, which resolved with treatment and without any sequalae.

In terms of washing versus not washing after thawing for the PD UCB transplants, data was available for the 84 patients in remission without history of prior transplants who received either washed (n=43) or non-washed (n=40) PD UCB units for HSCT. All PD cord blood units undergoing any kind of washing (e.g., dilution and centrifugation separation), regardless of the protocol, were grouped under the washed group. All PD cord blood units that were thawed and infused without a centrifugation step, whether or not diluted (e.g., reconstituted) prior to infusion were classified in the unwashed group. Adverse events of any grade occurring more than once during infusion included hemoglobinuria (9 unwashed, 1 washed), hypertension (6 unwashed, 4 washed), hives (1 unwashed, 1 washed), nausea/vomiting (2 unwashed), and dyspnea (1 unwashed, 1 washed). One unwashed patient developed seizures and encephalopathy that resolved without any sequelae, although the relationship to infusion was uncertain.

The total nucleated cell (TNC) recovery after thawing was higher for the unwashed group (median 95%) than for the washed group (median 75%). Unadjusted cumulative incidence of neutrophil engraftment was similar for both groups:

91±5% for unwashed (n=36) versus 93±4% for washed (n=41). However, the median time to neutrophil engraftment (20 vs. 26 days) and platelet engraftment (platelet 20K: 47 vs. 55 days; platelet 50K: 55 vs. 63 days) occurred earlier for the unwashed group. This difference was highly significant for the platelet engraftment speed in both univariate and multivariate analyses. This difference was also significant for the neutrophil engraftment speed in univariate analysis. Additionally, the cumulative incidence for platelet 20K engraftment was significantly higher for unwashed (n=28; 92±6%) than washed (n-39; 75±7%) for both univariate and multivariate analyses. Acute grade III-IV GvHD was 10% (unwashed) and 19% (washed), and extensive chronic GvHD was 0% (unwashed) and 22% (washed). TRM was 18±6% for unwashed and 20±7% for washed, with the relapse rate for malignant cases at 11±7% for unwashed and 25±8% for washed. One-year overall survival was 75±7% (n=40) versus 72±8% (n=43), and one-year DFS was 69±10% (n=23) versus 54±9% (n=34) for unwashed and washed, respectively.

With regard to hematopoetic stem cell transplantation for benign indications, the median time to engraftment for ANC500, platelet 20K, and platelet 50K for the washed group versus the unwashed group were 27 vs. 12 days, 58 vs. 44 days, and 73 vs. 53 days, respectively. With regard to hematopoetic stem cell transplantation for malignant indications, the median time to engraftment ANC500 and platelet 20K for the washed group versus the unwashed group were 28 vs. 23 days and 55 vs. 49 days, respectively.

FIG. 6 shows that, in a multivariate analysis, not washing significantly improved platelet engraftment when a total of 94 patients in remission without history of prior transplants received either washed (n=52) or non-washed (n=42) PD UCB units for HSCT. Overall, the adjusted analyses confirmed univariate results showing that non-washed transplants engrafted (P20K and P50K) sooner than washed units.

| Characteristics of Wash versus Non-wash Cases (n = 94) | | | |
|---|---|---|---|
| | Non-wash (n = 42, 45%) | Wash (n = 52, 55%) | P* |
| Recipient Factors | | | |
| Female | 19 (45%) | 19 (36%) | 0.41 |
| Age (yrs) | | | |
| 0-2 | 6 (14%) | 14 (27%) | 0.27 |
| 3-11 | 21 (50%) | 19 (36%) | |
| 12-18 | 5 (12%) | 10 (19%) | |
| 19-55 | 10 (24%) | 9 (17%) | |
| Double cords | 8 (19%) | 9 (17%) | 0.99 |
| Malignant | 26 (62%) | 45 (86%) | 0.008 |
| Transplant Factors | | | |
| High risk (yes) | 6 (14%) | 20 (38%) | 0.01 |
| Pre-Freeze TNC Dose × 10$^7$/kg | | | |
| <3 | 6 (14%) | 9 (17%) | 0.13 |
| 3-5 | 20 (48%) | 16 (31%) | |
| 6-9 | 4 (9%) | 14 (27%) | |
| >9 | 12 (28%) | 13 (25%) | |
| HLA 6-ag match | 7 (17%) | 8 (15%) | 0.99 |

*P-values computed using Fisher's Exact Tests

A follow-up study of 237 patients that included the 118 pediatric patients described above was performed. The median age was 9 years old (range 0.3-59), with 33%>16 years old; the median weight was 30 kg (range 4.5-112), with 35%>50 kg; 60% were male; the median # of HLA ABDR matches was 4.0; the median TNC dose was 5.6×10$^7$/kg; the median CD34 dose was 1.8×10$^5$/kg; the transplant center reported median post-thaw TNC dose was 5.2×10$^7$/kg; there were 70% malignant indications; 39% of the transplants were outside the U.S.; there were 27% double transplants; and 16% of the transplants were performed after non-myeloablative therapy. The incidence of grade III-IV aGVHD and extensive cGVHD were 13% and 14%, respectively. Unadjusted engraftment rate of ANC500, platelet 20K, and platelet 50K engraftment were 88±3%, 82±4% and 76±4%, respectively. The median time to engraftment for ANC 500, platelet 20K, and platelet 50K were 22, 48, and 63 days, respectively. The relapse rate was 23±4% and the TRM was 29±3%. With a median follow-up of 325 days, 1-year overall survival and disease-free survival were 59±4% and 54±4%, respectively. Stratification analysis showed worse engraftment and survival outcome at CD34+ cell dose below 0.7×10$^7$/kg.

There were 113 washed (W) and 95 non-washed (NW) PD cord blood transplantations. No significant adverse events occurred when the recommended DMSO threshold of 1 g per kg recipient weight was not exceeded. TNC recovery after thawing as reported by transplant centers was higher for NW (median 89% vs. 75%).

Unadjusted engraftment rates were higher and median times to engraftment were earlier for NW than W PD CB: 91±4% and 20 days for NW vs. 88±4% and 24 days for W for ANC500 (p=0.03); 86±6% and 44 days for NW vs. 78±5% and 58 days for W for platelet 20K (p=0.004); 85±6% and 57 days for NW vs. 72±6% and 75 days for W for platelet 50K (p=0.01). Acute grade III-IV GvHD incidences were 12% (NW) and 13% (W), and extensive chronic GvHD were 4% (NW) and 19% (W), respectively. Relapse rates were 16±5% for NW and 28±5% for W (p=0.15), with the TRM at 25±5% for NW and 34±5% for W (p=0.52). 1-year overall survival was 63±6% vs. 49±5% (p=0.40), and 1-year DFS was 62±6% vs. 36±7% for NW and W (p=0.21), respectively.

The outcome for PD cord blood transplantations compared favorably to published data of outcome using RBC depleted cord blood transplantations and trended better with respect to engraftment, TRM, and survival. There was no benefit to post-thaw washing of PD cord blood, and not washing was significantly better than post-thaw washing of PD cord blood with respect to neutrophil and platelet engraftment rate and speed to engraftment, TRM, relapse rate, 1-year overall survival, and DFS.

This example demonstrates the following: (1) PD UCB transplants have higher average and median cell dose; (2) the unadjusted cumulative incidence of neutrophil and platelet engraftment appear to be significantly better than red cell-depleted (RD) units for both children and adults; (3) outstanding speed of neutrophil and platelet engraftment, approaching that of bone marrow transplants for benign indications; (4) 1-year survival rate and transplant-related mortality rate are significantly improved versus RD units for both adults and children, especially benign indications for children; (5) relapse rate is as good as RD UCB transplants; and (6) not washing post-thaw PD UCB units improves engraftment significantly versus washing. As a result, this example illustrates that PD UCB transplantation can be performed safely in patients with results that are comparable or superior to historical controls. This example further shows that not washing PD UCB units after thawing improved the incidence to platelet engraftment and the time to engraftment for neutrophils and platelets, indicating that post-thaw washing delayed the engraftment of hematopoetic stem cells.

Example 5

Rapid and Durable Engraftment After Unrelated Cord Blood Transplantation for Children with Transfusion-Dependent Thalassemia This example illustrates that the cord blood compositions of the present invention, which provide optimal total nucleated cell dosage, produce rapid and durable engraftment in patients with transfusion-dependent thalassemia.

Umbilical cord blood (UCB) is an attractive unrelated source for hematopoietic stem cell transplantation of thalassemia. However, cell dosage is a critical factor for cord blood transplantation. In fact, cord blood transplantation has often been unsuccessful in the treatment of thalassemia because large numbers of transplanted cells need to be administered to sustain hematopoiesis and prevent rejection (Rund et al., *N. Engl. J. Med.* 353:1135-1146 (2005)). This example demonstrates that promising results can be achieved with unrelated cord blood transplantation in selected patients by maximizing cell dosage according to the methods of the present invention.

Between October 2003 and September 2005, unrelated cord blood transplantation was used for the hematopoietic reconstitution after myeloablative therapy in 10 pediatric patients with transfusion-dependent thalassemia (see, Table 5).

With 2 double unit transplants and 12 cord blood units for 10 patients, there were three 6/6, three 5/6, four 4/6, and two 3/6 high resolution HLA A/B/DR matches. All cord blood units were provided by StemCyte Taiwan National Cord Blood Center and were depleted of plasma but did not undergo red blood cell (RBC) depletion in order to achieve maximal retention of nucleated cells after volume reduction processing. To further enhance infused cell dose, all units were thawed and infused immediately without washing. Significant adverse events were not observed after infusion despite major ABO incompatibility in most cases. The median number of post-processing pre-freeze total nucleated cells (TNC) was $8.7 \times 10^7$/kg (range $4.8\text{-}15.0 \times 10^7$/kg) and the median number of post-processing pre-freeze CD34 cells was $4.1 \times 10^5$/kg (range $2.1\text{-}8.0 \times 10^5$/kg) of the recipient's body weight. No serious adverse events were associated with infusion. One patient died of penicillin-resistant *S. mitis* sepsis at day +8 prior to the "expected" time to neutrophil engraftment. The other 9 patients are alive and well with a median follow up time of 378 days as of Oct. 8, 2005. Eight patients with neutrophil engraftment showed full donor chimerism by day +21 and the remaining patient achieved stable mixed chimerism (85.6% donor's cells) by day 162 and is currently at day 311 days post-transplant. Autologous recovery was not seen in any of the patients.

The median times to neutrophil engraftment (absolute neutrophil count $\geq 500$ for three consecutive days), RBC transfusion independence, and platelet engraftment ($\geq$platelet count of 20,000 for 7 consecutive days without platelet transfusion) were 14 (range 12-24 days), 35 (range 20-50 days), and 51 days (range 45-60 days) after transplantation, respectively. The number of patients with grade I, II, and III acute graft versus host disease (GvHD) that resolved with treatment were three, four, and three respectively. No extensive chronic GvHD had developed at the latest contact.

Thirty-two percent of transfusion dependent thalassemia patients do not live past age 35 (Cao, *Haematologica* 89:1157-1158 (2004)). Several studies have demonstrated improved survival after cord blood transplantation using higher cell doses in different diseases (Wagner et al., *Blood*

TABLE 5

Cat Summaries

| Case # | Age in Years, Sex, & Weight | Lucarelli class[^] | HLA Match | TCN Dose ($\times 10^7$/kg) | CD34 Dose ($\times 10^5$/kg) | # Days to ANC 500 Engraftment | Acute GvHD Grade | Status Days post-CBT | # Days post-CBT Discharged | Latest Chrimerism at # Days post-CBT |
|---|---|---|---|---|---|---|---|---|---|---|
| 1 | 3.7/F 17 Kg | I | 5/6 | 11.3 | 2.4 | 17 | I | Alive 713 | 85 | 100% 557 |
| 2 | 2.3/F 12 Kg | I | 3/6 | 15.0 | 5.1 | 12 | II | Alive 604 | 80 | 100% 419 |
| 3 | 3.6/F 17 Kg | I | 3/6 | 13.4 | 2.1 | 14 | I | Alive 570 | 76 | 100% 410 |
| 4 | 5.8/M 18 Kg | | 4/6 | 5.3 | 3.4 | 12 | II | Alive 514 | 70 | 100% 378 |
| 5 | 11.4/M 30 Kg | I | 3/6 (unit 1) 3/6 (unit 2) | 11.3 (combined dose) | 5.7 (combined dose) | 12 | III | Alive 416 | 98 | 100% 285 |
| 6 | 8.2/F 21 Kg | I | 6/6 | 7.7 | 8.0 | NA | NA | Expired 8 | NA | NA |
| 7 | 6.5/F 23 Kg | I | 6/6 | 4.8 | 3.6 | 12 | II | Alive 339 | 46 | 100% 205 |
| 8 | 2.7/F 14 Kg | I | 5/6 | 7.6 | 2.9 | 24 | III | Alive 311 | 78 | 85.6% 162 |
| 9 | 3.3/F 15 kg | I | 6/6 | 9.6 | 5.5 | 18 | II | Alive 283 | 50 | 100% 109 |
| 10 | 9.5/M 38 kg | II | 5/6 (unil 1) 4/6 (unit 2) | 7.9 (combined dose) | 4.6 (combined dose) | 19 | I | Alive 82 | Still Inpatient | 91.6% I 5.6% II 42 |
| Mean | 5.6 yrs 20.5 Kg | | 4.6 | 9.4 | 4.3 | 15.6 | | 384 | 384 | 73 | 98.2 331.5% |
| Median | 4.8 yrs 17.5 Kg | | 4.5 | 8.7 | 4.1 | 14.0 | | 378 | 378 | 77 | 100% 315.5 |

[^]Patients at Chung Gung do not routinely undergo liver biopsy. Patients are classified based on the presence of 0, 1, or 2 of the remaining two features (hepatomegaly and poor chelation) of the Lucarelli classification.

100:1611-1618 (2002); Barker et al, *Blood* 105:1343-1347 (2005); Locatelli et al., *Blood* 93:3662-3671 (1999)). Unrelated UCB is a reasonable alternative to unrelated donor bone marrow, presuming that the unit contains sufficient cell dose. This study demonstrates that in the setting of adequate cell dosage, which can be maximized by the choice of double unit transplants and/or processing and thawing techniques, unrelated cord blood transplantation can produce rapid and durable engraftment in selected patients with transfusion-dependent thalassemia. The median hospital stay for this study is 77 days after transplantation (range 46 to 98 days), and is clearly cost-effective with improved quality of life when compared to conventional lifelong treatment with blood transfusions and iron chelation therapy.

In a follow-up study of 15 patients with transfusion-dependent thalassemia that included the 10 pediatric patients described above, unrelated cord blood transplantation using the cord blood compositions of the present invention produced rapid and durable engraftment (see, Table 6).

TABLE 6

Case Summaries.

| Pt # 1X or 2X CBT$^a$ | Age (yrs)/ sex, & weight | Lucarelli Class$^b$ | HLA Match$^c$ | TNC Dose$^d$ Discharge (×10$^7$/kg) | CD34 Dose$^e$ (×10$^5$/kg) | # Days to Neutrophil Engraftment$^f$ | # Days to Platelet 20K engraftment$^g$ | aGvHD cGvHD$^h$ | Status Days post-CBT$^i$ | # Days to Discharge | Chimerism post-CBT$^j$ |
|---|---|---|---|---|---|---|---|---|---|---|---|
| 1 1X | 3/F 17 Kg | I | 5/6 | 11.3 | 2.4 | 17 | 49 | I Ltd | Alive d925 | 75 | 100% d557 |
| 2 1X | 2/F 12 Kg | I | 3/6 | 15.0 | 5.1 | 12 | 46 | I Ltd | Alive d806 | 69 | 100% d419 |
| 3 1X | 3/F 17 Kg | I | 3/6 | 13.4 | 2.1 | 14 | 50 | I None | Alive d772 | 76 | 100% d410 |
| 4 1X | 5/F 16 kg | II | 4/6 | 5.1 | 4.4 | 23 | 66 | None None | Alive d728 | 46 | 100% d101 |
| 5 1X | 5/M 18 Kg | I | 4/6 | 5.3 | 3.4 | 12 | 43 | II Ltd | Alive d716 | 58 | 100% d671 |
| 6 2X | 11/M 30 Kg | I | 3/6 (1) 3/6 (2) | 11.3$^k$ (combined) | 5.7$^k$ (combined) | 12 | 55 | II Ltd | Alive d618 | 86 | 100% (1) d285 |
| 7 1X | 8/F 21 Kg | I | 6/6 | 7.7 | 8.0 | NA | NA |  | Expired$^l$ d8 | NA | NA |
| 8 1X | 6/F 23 Kg | I | 6/6 | 4.8 | 3.6 | 11 | 47 | I Ltd | Alive d541 | 44 | 100% d376 |
| 9 1X | 2/F 14 Kg | I | 5/6 | 7.6 | 2.9 | 21 | 50 | II Ltd | Alive d513 | 78 | 72.7% d365 |
| 10 1X | 3/F 15 kg | I | 6/6 | 9.6 | 5.5 | 18 | 43 | I Ltd | Alive d485 | 50 | 100% d109 |
| 11 2X | 9/M 38 kg | II | 5/6 (1) 4/6 (2) | 7.9$^k$ (combined) | 4.6$^k$ (combined) | 19 | 68 | I None | Alive d284 | 82 | 100% (1) d100 |
| 12 1$^{st}$ - 1X$^m$ 2$^{nd}$ - 2X | 7/F 21 kg | I | 1$^{st}$ - 3/6 2$^{nd}$ - 5/6 (1) 2$^{nd}$ - 4/6 (2) | 1$^{st}$ - 7.7 2$^{nd}$ - 18.0$^k$ (combined) | 1$^{st}$ 3.3 2$^{nd}$ - 5.5$^k$ (combined) | 1$^{st}$ - Graft Failure 2$^{nd}$ - 20 | NA | IV None | Expired$^n$ d60 | NA | 2$^{nd}$ 100% d48 |
| 13 2X | 10/M 30 kg | II | 4/6 (1) 4/6 (1) | 14.7$^k$ (combined) | 6.5$^k$ (combined) | 19 | 135 | III Ext | Alive d207 | 137 | 100% d193 |
| 14 1X | 9 M 20 kg | I | 4/6 | 5.5 | 3.6 | 16 | 34 | III None | Alive d72 | NA | 100% d60 |
| 15 2X | 11 F 33 kg | I | 4/6 (1) 4/6 (1) | 11.7$^k$ (combined) | 5.5$^k$ (combined) | 14 | 28 | I None | Alive d39 | 36 | 100% (1) d42 |
| Mean | 7 yrs old 22 kg | | 4.4 | 9.4 | 4.2 | 16 | 55 | | 461 (526°) | 70 | |
| Median | 6 yrs old 20 kg | | 4.0 | 7.8 | 3.9 | 17 | 49 | | 523 (551°) | 72 | |

$^a$1XCBT = single unit cord blood transplant; 2XCBT = double unit cord blood transplant.
$^b$Patients are classified based on the presence of 0, 1, or 2 of two features (hepatomegaly and poor chelation) of the Lucarelli classification.
$^c$HLA matches are at high resolution with (1) and (2) representing the number of HLA matches for the first and second cord blood unit.
$^d$TNC = total nucleated cell.
$^e$CD34 = CD34+ cells.
$^f$# days to neutrophil engraftment is the first of 3 consecutive days reaching an absolute neutrophil count ≧ 500 - 14 of 16 transplants (88%) achieved engraftment and exhibited durable donor chimerism resulting in a Kaplan-Meier engraftment rate of 93 ± 6%.
$^g$# days to platelet engraftment is the first of 7 consecutive days reaching platelet count of ≧ 20,000 or 50,000 for 7 consecutive days without platelet transfusion - Kaplan-Meier estimate of platelet 20K and 50K engraftment rate is 91 ± 9% and 82 ± 8%, respectively.
$^h$aGvHD = acute graft-versus-host disease with grades from I-IV; cGvHD = chronic graft-versus-host disease, graded either as limited (Ltd) or as extensive (Ext).
$^i$Follow-up as of May 8, 2006.
$^j$Latest donor chimerism data with the engrafting unit in brackets.
$^k$Combined cell dose of both cord blood units in a double unit cord blood transplants.
$^l$Patient 7 expired at day +8 from penicillin-resistant *S. mitis* sepsis.
$^m$Patient 12 failed an initial 3/6 HLA matched cord blood transplant, but engrafted with a double unit cord blood transplant subsequently.
$^n$Patient 12 expired at day +60 after achieving engraftment from a traumatic accident causing intracranial hemorrhage.
$^o$Mean and median follow-up time, excluding expired patients.

Frozen cord blood units that were substantially depleted of plasma, but not of red blood cells were thawed and infused without washing to maximize cell dose. Significant adverse events were not observed despite ABO incompatibility. After myeloablation, 21 cord blood units were transplanted into 15 Asian thalassemia major patients, with 5 double unrelated cord blood transplants and one re-transplant. Despite 86% of cord blood unit-recipient pairs with HLA mismatches, few had serious GvHD; all resolved with treatment. Unadjusted cumulative incidence of neutrophil engraftment with donor chimerism was 93±6%. Median times to achieve neutrophil engraftment, RBC transfusion independence, and platelet engraftment were 16, 35, and 46 days, respectively. Thalassemia-free survival was 87±9%, 1-year overall survival was 86±9%, transplant related mortality at 1-year was 13±9%, and the relapse rate was 0%. Since 68% of thalassemia major patients live past age 35 and most have no HLA-matched siblings, unrelated cord blood transplantation produces satisfactory survival and provides a cost-effective alternative with improved quality of life compared to lifelong transfusion and chelation.

Example 6

An Audited Matched Pair Analysis of Transplants Using Red Cell-Depleted Versus Plasma-Depleted Umbilical Cord Blood Units This example illustrates a procedure for performing a matched pair analysis between PD and red blood cell-depleted (RD) UCB transplants to determine the significant differences in clinical outcome between hematopoetic stem cell transplantation conducted with PD UCB versus RD UCB.

A matched pair retrospective analysis is probably the most definitive retrospective method to determine the significant differences in clinical outcome between HSCT conducted with PD UCB versus RD UCB. To perform the matched pair analysis between PD and RD UCB transplants, patients transplanted with RD or PD UCB units can be matched and paired according to the following priorities: (1) recipient age (±2 years for patients under 16 and ±5 years for patients over 16); (2) weight (±5 kg for patients under 50 kg and 110 kg for patients over 50 kg); (3) diagnosis; (4) degree of HLA match; (5) prior transplant or transplanted during relapse, induction failure, or resistant disease; (6) risk status for malignancies and certain diseases (e.g., for leukemia: CR# or CP# and degree of risk as evidenced by known prior diagnosis of myelodysplasia (MDS), high-risk cytogenetics such as those with t(9;22), t(1:19), t(4;11), or other MLL rearrangements, or complex karyotype associated with MDS; for lympomas: grade of lymphoma should be matched; for thalassemias: Pesaro class should be matched); (7) optionally single versus double cord blood units (in the case of double unit transplants, both units should be processed the same way); and (8) optionally myeloablation versus reduced intensity. If multiple RD UCB transplant recipients are matched with a PD UCB transplant recipient, then preference is given to the RD UCB recipient with the closest weight followed by the closest year of transplantation. If an RD UCB transplant patient cannot be matched with regards to all of the above criteria to a PD UCB recipient, then preference is given to the RD UCB patient that can be matched according to the top priorities, starting from the first priority. Preference is not given to the number of priorities matched. For example, the RD UCB patient that matched with the top five priorities can be given preference over the RD UCB patient that matches with the top four priorities plus priorities 6, 7, and 8.

Patients can also be analyzed as follows:

(1) Because the two types of processing differ theoretically in the degree of nucleated cell recovery post-processing, which may ultimately affect average and median cell dose of such transplants and ultimately clinical outcome, nucleated and CD34 cell dose would not be matched initially. If significant differences are seen between PD and RD units, then matched pairs with similar (a) nucleated ($\pm 0.5 \times 10^7$/kg of each other) or (b) CD34+ cell dose ($\pm 0.25 \times 10^5$/kg of each other) can be compared with pairs without similar cell dose. It is reasoned that if a statistically significant difference is observed between the two types of cord blood, and cell dose is the principal reason, then the pairs matched in cell dose should have less difference in clinical outcome between PD and RD units than pairs that are unmatched in cell dose. Alternatively, if outcome differences exist between PD and RD units for both dose matched pairs and dose unmatched pairs, then cell dose may not be the only mechanism accounting for the difference in clinical outcome. Cell dose stratification of both PD and RD groups can be used to see if there are any differences when cell doses are matched.

(2) For malignancies, transplant pairs without prior transplants and performed during remission can be contrasted with pairs with prior transplant and/or performed during relapse, induction failure, or with resistant disease. If possible, the two cohorts of patients could be compared for (1) gender, (2) CMV sero-positivity, (3) graft pre-freeze or cryopreservation and post-thaw nucleated and CD34+ cell dose, (4) year of transplantation, (5) median follow up, (6) time from diagnosis to transplants; (7) region of transplant (U.S., Western Europe, Australia, Central or South America, Asia), and, if available, (8) conditioning regimen.

For the matched pair analysis between PD and RD UCB units, the following study endpoints can be used:

I. Primary Outcome:
1. Overall survival at 12 months post-transplant.
2. Unadjusted cumulative incidence of sustained neutrophil engraftment (unadjusted for deaths prior to the expected engraftment period).
3. Speed of sustained neutrophil engraftment.

II. Secondary Outcome:
1. Disease free survival at 12 months post-transplant.
2. TRM at 12 months post-transplant.
3. Unadjusted cumulative incidence of sustained platelet engraftment (unadjusted for deaths prior to the expected engraftment period).
4. Speed of sustained platelet engraftment.
5. The incidence and severity of acute and chronic graft-versus-host disease (GVHD).
6. The incidence of malignant relapse.
7. The incidence and severity of post-infusion adverse events.

Example 7

Procedure for Thawing and Direct Infusion of Frozen Umbilical Cord Blood Units

This example describes a protocol for thawing and direct infusion of the plasma-depleted, cryopreserved cord blood units of the present invention without performing any washing steps.

In instances where patients are not neonates and do not have compromised renal function, the following protocol may be preferred because it minimizes viable nucleated cell loss inevitable with washing and prolonged manipulation after thawing. This approach produces favorable tolerance in patients with only occasional side-effects that can be easily treated with standard measures. As a result, the highest dose of viable stem cells can be safely and effectively infused into patients in need thereof.

Notes Before Thawing:

| Step | Action |
|---|---|
| 1 | Thaw the cord blood unit at the patient's bedside, if possible. The patient should be pre-medicated according to the usual practice at the transplant center, taking into consideration the amount of DMSO (7.5 to 15 g) and free hemoglobin in the unit as well as the potential for ABO/Rh incompatible red blood cells in the unit. |
| 2 | Transport the frozen cord blood unit to the patient's bedside in a validated liquid nitrogen storage container that will maintain the product at a temperature of ≦−135° C. |
| 3 | Before the cord blood product is thawed, verify the identity of the patient and the cord blood unit. |
| 4 | Occasionally, the cord blood unit may be in 2 freezing bags or two cord blood units are being employed in a double unit transplant. Only 1 bag should be thawed at a time and infusion of the first bag should be completed with the patient in a stable condition before thawing the other bag. Likewise, infusion of the bag(s) of the first cord blood unit should be completed with the patient in a stable condition prior to the thawing of the bag(s) of the second cord blood unit. |
| 5 | Perform testing of the cord blood unit using an attached segment or the residual left in the bag after the unit has been infused. |
| 6 | Once thawed, the cord blood unit must be infused immediately. Do not refreeze the cord blood unit once it has been thawed or partially thawed. |

Thawing the Cord Blood Unit:

| Step | Action |
|---|---|
| 1 | Fill a water bath with enough sterile water to completely immerse the umbilical cord blood unit. |
| 2 | Allow the water to come to a temperature of 37° C. ± 2° C. The water in the water bath should maintain this temperature throughout the thaw procedure |
| 3 | Tape a plastic bag (preferably sterile) to the side of the water bath. If the bag can be sealed, do not put it in the water bath yet. This bag is used to salvage the cord blood unit in case the freezing bag housing the cord blood unit is damaged, resulting in leakage. |
| 4 | Carefully remove the frozen unit from the metal cassette, verify the identification of the unit, and inspect the bag for any breakage. |
| 5 | Put the frozen cord blood unit into the plastic bag in order to prevent the cord blood unit from coming in direct contact with the water. For unsealed bags, gently knead the cord blood from the outside of the plastic bag, being careful not to get water into the bag. |
| 6 | For sealed bags, thaw the cord blood unit by sealing the bag after expressing most of the air, immersing it in the water, and gently kneading the cord blood unit through the plastic bag. |
| 7 | Do not leave the cord blood unit unattended at any time during the thaw procedure. |
| 8 | Check the cord blood bag for leaks as it thaws. If there are leaks, follow internal protocols for infusion of products with breaks or leaks and monitoring and prophylaxis antimicrobial treatment of patients infused with a potentially contaminated product. Do not discard the cord blood, especially if the transplant recipient has been conditioned. |
| 9 | Remove the cord blood unit from the water bath as soon as it is slightly "slushy," and not fully thawed. Take out the freezing bag from the outer plastic bag and disinfect the infusion ports with alcohol wipes. |

Infusion:

| Step | Action |
|---|---|
| 1 | Immediately and as quickly as possible draw up the product in a sterile 60 cc syringe through one of the disinfected ports of the freezing bag using the widest bore needle possible to minimize cell shearing. If there was leakage into the outer plastic bag, carefully remove the freezing bag from the outer bag, draw up any remaining product left in the freezing bag through the disinfected infusion port, and then carefully draw up the leaked product from the outer plastic bag |
| 2 | The product in the syringe is then immediately IV pushed through a central line as rapidly as possible (e.g., 5-10 ml/min). Because of the viscosity of the cord blood product, considerable resistance is to be expected. |
| 3 | The freezing bag can be rinsed with 10 to 20 cc of a 8% dextran/5% human serum albumin solution. |
| 4 | Thaw the second cord blood bag, if applicable, only after the first bag has been completely infused. |

Potential Adverse Reactions Associated with Hematopoietic Stem Cell Administration:

Mild to Moderate:

Frequent: nausea, vomiting, hypertension, hypotension, bradycardia, hemoglobinuria, shivering, sweet cream corn or garlic taste (from DMSO expiration).

Less frequent: headache, abdominal cramps, diarrhea, flushing, chills, fever, flushing, chest tightness, vertigo, encephalopathy, seizure, bradycardia, hyperbilirubinemia, increased serum transaminase levels.

Severe to Life Threatening:

Very rare (~0.4% in the largest published study of 1,410 patients) and usually self limited.

Cardiac: bradycardia, heart block, arrhythmia, shock, cardiac arrest.

Neurologic: encephalopathy (possibly related to greater than 2 g DMSO/kg recipient weight and treatable by plasmapheresis), seizure.

Pulmonary: respiratory depression

Immunologic: anaphylactic reaction

Renal: acute renal failure due to high concentration of free hemoglobin (mitigated by pre-medication with antihistamine and corticosteroid, adequate hydration, urinary alkalization, mannitol diuresis).

Causes of Potential Adverse Reactions:

DMSO Toxicity: Though the acute toxic dose of DMSO for humans has not been determined, the LD50 value (i.e., amount of DMSO required to kill 50% of the test animals) reported for IV administration of DMSO is between 3.1-9.2 g/kg for mice, 2.5/kg for dogs, and greater than 11 g/kg for monkeys. Most published reports have kept the DMSO dose below 1 g/kg. In a typical cord blood unit of the present invention, the maximal DMSO dose is between about 7.5 (1 bag) to about 15 g (2 bags). Therefore, in patients with compromised renal functions and in small patients (e.g., those under 7 kg for 1 bag and under 15 kg if two bags are to be administered at the same time), where achieving an adequate cell dose is not a problem, washing of the product is recommended. The preferred rate of infusion of a 10% DMSO cryopreserved stem cell product should be between about 5 to about 10 ml per minute.

Volume Overload: The maximal volume to be transfused should be in the range of about 5 to about 15 ml/kg/dose.

Major ABO Blood Group Incompatibility: Although ABO blood group incompatibility between patient and donor has not been an issue in cord blood transplantation, the following additional information is supplied in cases of major blood group incompatibility, e.g., patient is blood group O and the cord blood unit is not group O. Although transfusion of large volumes of major ABO incompatible red blood cells is known to cause transfusion reactions in patients who have a significant titer of anti-A and/or anti-B, Bensinger et al., *Transplantation* 33:427-429 (1982), noted that when the recipient's anti-A and anti-B hemagglutinin titers are 1:16 or less, entire units of ABO incompatible red blood cells may be transfused safely. Sauer-Heilbom et al., *Transfusion* 44:907-916 (2004), describes experience with transfusion of ABO incompatible peripheral blood stem cells (PBSC) and marrow units and noted that the risk is lower with PBSC units (red blood cell volume=75-100 ml) compared to bone marrow components (red blood cell volume=300-400 ml). The volume of red blood cells in the cord blood units of the present invention is about 40 to about 100 ml. This volume of red blood cells is not known to cause serious adverse effects, but symptoms such as elevated temperature, increased pulse, and muscle aching may occur. Dark or red urine and plasma are to be expected because of the hemolysis in the cord blood sample. The rate of infusion should be about 5 to about 10 ml/minute, with close patient monitoring. In certain instances, the patient can be pre-medicated with antipyretics, antihistamines, and/or corticosteroids and should be well hydrated. Adverse reactions usually occur during the infusion and resolve after the infusion is stopped. However, some reactions can occur about 6 to 7 hours after the completion of the infusion, so patients should be monitored throughout that time period.

Common pre-medication regimens include, but are not limited to, adequate hydration (e.g., major ABO mismatch), antihistamines (e.g., major ABO mismatch), corticosteroids, mannitol, antiemetics, and antipyretics (e.g., major ABO mismatch). Non-limiting examples of common therapeutic interventions for adverse events include diuretics (e.g., volume overload), anticonvulsants (e.g., seizures), atropine (e.g., bradycardia), plasmapheresis (e.g., encephalopathy), $O_2$ (e.g., pulmonary depression), and narcotics.

Example 8

Procedure for Thawing, Reconstitution, and Infusion of Frozen Umbilical Cord Blood Units This example describes a protocol for thawing, reconstitution, and infusion of the plasma-depleted, cryopreserved cord blood units of the present invention.

In certain situations where volume overload is not a serious consideration, to reduce the viscosity of the cord blood units of the present invention and facilitate gravity mediated IV infusion, the units can be diluted or reconstituted with, for example, about twice the volume of a human serum albumin/Gentran® solution according to the following protocol. This reduces the DMSO concentration of the post-diluted unit and any potential DMSO-induced toxicity to stem cells, and also allows more time between thawing and infusion. Its advantages include ease of administration and prolonged time for administration.

Notes Before Thawing:

| Step | Action |
|---|---|
| 1 | Thaw the frozen cord blood unit in a biological safety cabinet. |
| 2 | The patient should be pre-medicated according to the usual practice at the transplant center, taking into consideration the amount of DMSO (7.5 to 15 g) and free hemoglobin in the unit as well as the potential for ABO/Rh incompatible red blood cells in the unit. |
| 3 | Before the cord blood unit is thawed, verify the identity of the patient and the cord blood unit. |
| 4 | Occasionally, the cord blood unit may be in 2 freezing bags, or two cord blood units are being employed in a double unit transplant. Only 1 bag should be thawed at a time and infusion of the first bag should be completed with the patient in a stable condition before thawing the other bag. Likewise, infusion of the bag(s) of the first unit should be completed with the patient in a stable condition prior to thawing the bag(s) of the second cord blood unit. |
| 5 | Perform testing of the cord blood unit using an attached segment or the residual left in the bag after the unit has been infused. |
| 6 | Once thawed, the cord blood unit must be diluted or reconstituted immediately. Do not refreeze the cord blood unit once it has been thawed or partially thawed. |
| 7 | The Reconstitution Bag should be weighed. |

Preparation of Human Serum Albumin/Gentran® Reconstitution Solution:

| Step | Action |
|---|---|
| 1 | Close all roller clamps on thawing bag set and both plasma transfer sets. |
| 2 | Spike an injection port of bag #1 of the thawing bag set with one end of a plasma transfer set. |
| 2 | Remove the cap and clean the rubber diaphragm of a 50 ml vial of human serum albumin (HSA) with an alcohol prep. |
| 3 | Spike the HSA diaphragm with the other end of the plasma transfer set. |
| 4 | Insert a hypodermic needle into the HSA diaphragm next to the plasma spike to vent the vial. |
| 5 | For cord blood volumes of 100 ml or less:<br>Raise the HSA vial above bag #1, open roller clamp, and allow the entire contents of the vial (50 ml) to flow into bag #1.<br>For cord blood volumes greater than 100 ml:<br>Use 2 vials of HSA (100 ml aggregate) and add both to bag #1. |
| 6 | Heat seal the tubing between the HSA vial and bag #1 near the injection port of bag #1. Discard the HSA vial and excess tubing. |
| 7 | Spike the remaining injection port of bag #1 with the second plasma transfer set. |
| 8 | Spike the injection port of the Gentran ® 40 bag with the other end of the plasma transfer set. |
| 9 | Place bag #1 on the electronic scale and tare to zero. |
| 10 | For cord blood volumes of 100 or less:<br>Open roller clamp and allow 200 grams of Gentran ® 40 to run into bag #1.<br>For cord blood volumes greater than 100 ml:<br>Open roller clamp and allow 400 grams of Gentran ® 40 to run into bag #1. |
| 11 | Heat seal the plasma transfer tubing near bag #1 and discard the tubing. |
| 12 | The final volume in bag #1 should be either 250 ml or 500 ml (with a final concentration of 5% for HSA and 8% for Gentran ®). |
| 13 | Label bag #1 with the date and time that the wash was prepared and initials of the tech preparing the wash. |
| 14 | Record the unit number of the frozen cord blood unit, or place a unit identification label, on each of the 3 bags of the thawing bag set. |
| 15 | Place the thawing bag set with the wash solution into a 2° C. to 8° C. refrigerator to chill for at least 30 minutes. Once the wash solution is prepared, it should be used within 24 hours. |

Thawing the Cord Blood Unit:

| Step | Action |
|---|---|
| 1 | Fill a water bath with enough sterile water to completely immerse the umbilical cord blood unit. |
| 2 | Allow the water in the water bath to come to a temperature of 37° C. ± 2° C. The water in the water bath must maintain this temperature throughout the thaw procedure. |
| 3 | Tape a plastic bag (preferably sterile) to the side of the water bath. If the bag can be sealed, do not put it in the water bath yet. This bag is used to salvage the cord blood unit in case the freezing bag housing the cord blood unit is damaged, resulting in leakage. |
| 4 | Carefully remove the frozen unit from the metal cassette, verify the identification of the unit, and inspect the bag for any breakage. |
| 5 | Put the frozen cord blood unit into the plastic bag in order to prevent the cord blood unit from coming in direct contact with the water. This step should be performed as soon as the unit is removed from the liquid nitrogen and after verification of the identity and inspection of the unit. For unsealed bags, gently knead the cord blood from the outside of the plastic bag, being careful not to get water into the bag. If breakage of the freezing bag is observed, it is critical that contamination is minimized since contents of the bag will likely leak into the outside plastic bag. |
| 6 | For sealed bags, thaw the cord blood unit by sealing the bag after expressing most of the air, immersing it in the water, and gently kneading the cord blood unit through the plastic bag. |
| 7 | Do not leave the cord blood unit unattended at any time during the thaw procedure. |
| 8 | Check the cord blood bag for leaks as it thaws. If there are leaks, follow internal protocols for infusion of products with breaks or leaks and monitoring and prophylaxis antimicrobial treatment of the patients infused with a potentially contaminated product. Do not discard the cord blood. |
| 9 | Remove the cord blood unit from the water bath as soon as it is in a "icy slushy" state. Take out the freezing bag from the outer plastic bag and disinfect the infusion ports with alcohol wipes. This thawing step should not take longer than 5 minutes |

Cord Blood Product Dilution or Reconstitution:

| Step | Action |
|---|---|
| 1 | Immediately and as quickly as possible draw up the product in a sterile 60 cc syringe through one of the disinfected ports of the freezing bag using the widest bore needle possible to minimize cell shearing. If there was leakage into the outer plastic bag, carefully remove the freezing bag from the outer bag, draw up any remaining product left in the freezing bag through the disinfected infusion port, and then carefully draw up the leaked product from the outer plastic bag. |
| 2 | The cord blood product in the syringe is then immediately pushed into the Reconstitution Bag as rapidly as possible. Because of the viscosity of the cord blood product, considerable resistance is to be expected. |
| 3 | The Reconstitution Bag with the cord blood product is now weighed and the weight and volume of the thawed cord blood product from the difference between the weight with the product and the weight of the empty Reconstitution Bag is determined. |
| 4 | Twice the volume of a 5% Human Serum Albumin/8% Dextran (HSA/Gentran ®) Reconstitution solution is then added to the Reconstitution Bag. The dilution should not take longer than 5 minutes. For example, if the cord blood unit has a thawed volume of 75 cc or thawed weight of 75 g, then 150 cc of the HSA/Gentran ® Reconstitution Solution is added. |
| 5 | The reconstitution step should not take longer than 5 minutes to complete. |

Infusion:

| Step | Action |
|---|---|
| 1 | Immediately and as quickly as possible bring the unit up to the patient's room and infuse the product through a central line by hanging of the Reconstitution Bag. The thawed and reconstituted product should be infused within about 30 minutes. If the product is too viscous and will not flow well, push the product gently and slowly to help infusion. |
| 2 | Thaw the second cord blood bag, if applicable, only after the first bag has been completely infused and patient stability and tolerance have been ascertained. |
| 3 | From thawing to transport to infusion, the entire process should not take longer than 60 minutes. |

Potential Adverse Reactions Associated with Hematopoietic Stem Cell Administration:
 Mild to Moderate:
  Frequent: nausea, vomiting, hypertension, hypotension, bradycardia, hemoglobinuria, shivering, sweet cream corn or garlic taste (from DMSO expiration).
  Less frequent: headache, abdominal cramps, diarrhea, flushing, chills, fever, flushing, chest tightness, vertigo, encephalopathy, seizure, bradycardia, hyperbilirubinemia, increased serum transaminase levels.
 Severe to Life Threatening:
  Very rare (~0.4% in the largest published study of 1,410 patients) and usually self limited.
  Cardiac: bradycardia, heart block, arrhythmia, shock, cardiac arrest.
  Neurologic: encephalopathy (possibly related to greater than 2 g DMSO/kg recipient weight and treatable by plasmapheresis), seizure.
  Pulmonary: respiratory depression
  Immunologic: anaphylactic reaction
  Renal: acute renal failure due to high concentration of free hemoglobin (mitigated by pre-medication with antihistamine and corticosteroid, adequate hydration, urinary alkalization, mannitol diuresis).
Causes of Potential Adverse Reactions:
 DMSO Toxicity: Though the acute toxic dose of DMSO for humans has not been determined, the LD50 value (i.e., amount of DMSO required to kill 50% of the test animals) reported for IV administration of DMSO is between 3.1-9.2 g/kg for mice, 2.5/kg for dogs, and greater than 11 g/kg for monkeys. Most published reports have kept the DMSO dose below 1 g/kg. In a typical cord blood unit of the present invention, the maximal DMSO dose is between about 7.5 (1 bag) to about 15 g (2 bags). Therefore, in patients with compromised renal functions and in small patients (e.g., those under 7 kg for 1 bag and under 15 kg if two bags are to be administered at the same time), where achieving an adequate cell dose is not a problem, washing of the product is recommended. The preferred rate of infusion of a 10% DMSO cryopreserved stem cell product should be between about 5 to about 10 ml per minute.
 Volume Overload: The maximal volume to be transfused should be in the range of about 5 to about 15 ml/kg/dose.
 Major ABO Blood Group Incompatibility: Although ABO blood group incompatibility between patient and donor has not been an issue in cord blood transplantation, the following additional information is supplied in cases of major blood group incompatibility, e.g., patient is blood group O and the cord blood unit is not group O. Although transfusion of large volumes of major ABO incompatible red blood cells is known to cause transfusion reactions in patients who have a significant titer of anti-A and/or anti-B, Bensinger et al., *Transplantation* 33:427-429 (1982), noted that when the recipient's anti-A and anti-B hemagglutinin titers are 1:16 or less, entire units of ABO incompatible red blood cells may be transfused safely. Sauer-Heilbom et al., *Transfusion* 44:907-916 (2004), describes experience with transfusion of ABO incompatible peripheral blood stem cells (PBSC) and marrow units and noted that the risk is lower with PBSC units (red blood cell volume=75-100 ml) compared to bone marrow components (red blood cell volume=300-400 ml). The volume of red blood cells in the cord blood units of the present invention is about 40 to about 100 ml. This volume of red blood cells is not known to cause serious adverse effects, but symptoms such as elevated temperature, increased pulse, and muscle aching may occur. Dark or red urine and plasma are to be expected because of the hemolysis in the cord blood sample. The rate of infusion should be about 5 to about 10 ml/minute, with close patient monitoring. In certain instances, the patient can be pre-medicated with antipyretics, antihistamines, and/or corticosteroids and should be well hydrated. Adverse reactions usually occur during the infusion and resolve after the infusion is stopped. However, some reactions can occur about 6 to 7 hours after the completion of the infusion, so patients should be monitored throughout that time period.

Common pre-medication regimens include, but are not limited to, adequate hydration (e.g., major ABO mismatch), antihistamines (e.g., major ABO mismatch), corticosteroids, mannitol, antiemetics, and antipyretics (e.g., major ABO mismatch). Non-limiting examples of common therapeutic interventions for adverse events include diuretics (e.g., volume overload), anticonvulsants (e.g., seizures), atropine (e.g., bradycardia), plasmapheresis (e.g., encephalopathy), $O_2$ (e.g., pulmonary depression), and narcotics.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications, patents, and PCT publications, are incorporated herein by reference for all purposes.

What is claimed is:

1. A composition comprising anticoagulated plasma-depleted umbilical cord blood and a cryoprotectant,
   wherein the anticoagulated plasma-depleted umbilical cord blood is not depleted in red blood cells when compared to whole blood umbilical cord blood,
   wherein the anticoagulated plasma-depleted umbilical cord blood is at least 50% red blood cells by volume, and
   wherein the anticoagulant is about 5% to about 40% by volume of the plasma-depleted umbilical cord blood.

2. The composition of claim 1, wherein said anticoagulated plasma-depleted umbilical cord blood comprises at least 65% red blood cells by volume.

3. The composition of claim 1, wherein said anticoagulated plasma-depleted umbilical cord blood comprises from 0% to about 30% plasma by volume.

4. The composition of claim 1, wherein said anticoagulated plasma-depleted umbilical cord blood comprises stem cells.

5. The composition of claim 4, wherein said stem cells are hematopoietic stem cells.

6. The composition of claim 1, wherein said anticoagulated plasma-depleted umbilical cord blood comprises from about 5% to about 20% by volume of said anticoagulant.

7. The composition of claim 1, wherein said anticoagulant is selected from the group consisting of citric acid, sodium citrate, and mixtures thereof.

8. The composition of claim 1, wherein said cryoprotectant is dimethyl sulfoxide (DMSO).

9. The composition of claim 1, wherein said cryoprotectant is a mixture of DMSO and Gentran® 40.

10. The composition of claim 1, wherein said cryoprotectant is a mixture of DMSO and hydroxyethyl starch (HES).

11. The composition of claim 1, wherein said composition comprises a red blood cell concentration of from about $3.2 \times 10^6$ to about $8 \times 10^6$ red blood cells/μl.

12. The composition of claim 1, wherein said composition comprises a white blood cell concentration of greater than $10 \times 10^6$ white blood cells/ml.

13. The composition of claim 1, wherein said composition comprises a CD34+ cell number of from 2.1 to $8.0 \times 10^5$/kg of a mammalian subject's body weight.

14. The composition of claim 1, wherein said composition comprises a total nucleated cell number of from $4.8 \times 10^7$ to $15.0 \times 10^7$/kg of a mammalian subject's body weight.

15. A method for preparing a composition of claim 1, said method comprising:
   removing a volume of plasma from an anticoagulated umbilical cord blood sample to form the anticoagulated plasma-depleted umbilical cord blood sample, and then
   adding a cryoprotectant to the anticoagulated plasma-depleted umbilical cord blood sample to form a mixture.

16. The method of claim 15, wherein said anticoagulant is selected from the group consisting of citric acid, sodium citrate, and mixtures thereof.

17. The method of claim 15, wherein said cryoprotectant is dimethyl sulfoxide (DMSO).

18. The method of claim 15, wherein said cryoprotectant is a mixture of DMSO and Gentran® 40.

19. The method of claim 15, wherein said cryoprotectant is a mixture of DMSO and hydroxyethyl starch (HES).

20. The method of claim 15, further comprising:
   lowering the temperature of the anticoagulated plasma-depleted umbilical cord blood sample and cryoprotectant mixture at a rate of about −1° C. per minute from about 4° C. to about −50° C.

21. The method of claim 20, further comprising:
   lowering the temperature of the anticoagulated plasma-depleted umbilical cord blood sample and cryoprotectant mixture at a rate of about −10° C. per minute from about −50° C. to about −90° C.

22. The method of claim 21, further comprising:
   storing the anticoagulated plasma-depleted umbilical cord blood sample and cryoprotectant mixture below about −135° C.

23. The method of claim 22, further comprising:
   thawing the stored anticoagulated plasma-depleted umbilical cord blood sample and cryoprotectant mixture.

24. The composition of claim 1, wherein said anticoagulant is a mixture of citric acid, sodium citrate, sodium phosphate, and dextrose.

25. The composition of claim 1, wherein said cryoprotectant comprises from about 5% to about 15% by volume of DMSO.

26. The composition of claim 25, wherein said cryoprotectant further comprises Gentran® 40.

27. The composition of claim 1, wherein said cryoprotectant is glycerol.

28. The composition of claim 1, wherein said anticoagulant is a mixture of citric acid, sodium citrate, sodium phosphate, dextrose, and adenosine.

29. The method of claim 15, wherein said anticoagulant is a mixture of citric acid, sodium citrate, sodium phosphate, and dextrose.

30. The method of claim 15, wherein said anticoagulant is a mixture of citric acid, sodium citrate, sodium phosphate, dextrose, and adenosine.

* * * * *